United States Patent [19]
Russo-Rodriguez et al.

[11] Patent Number: 5,864,031
[45] Date of Patent: Jan. 26, 1999

[54] PROCESS FOR PREPARING 5-DITHIO-MODIFIED OLIGONUCLEOTIDES

[75] Inventors: Sandra E. Russo-Rodriguez, Superior; Tepper M. Koga, Louisville, both of Colo.

[73] Assignee: Amgen Inc., Thousand Oaks, Calif.

[21] Appl. No.: 282,383

[22] Filed: Jul. 29, 1994

[51] Int. Cl.$^6$ .............................. C07H 1/02; C07H 21/00; C07H 21/04
[52] U.S. Cl. ........................................ 536/25.34; 536/25.3
[58] Field of Search ................................ 536/25.3, 25.34

[56] References Cited

U.S. PATENT DOCUMENTS

| | | | |
|---|---|---|---|
| 3,687,808 | 8/1972 | Merrigan et al. | 536/25.5 |
| 4,587,241 | 5/1986 | Girijavallabhan et al. | 514/192 |
| 5,218,088 | 6/1993 | Gorenstein et al. | 536/25.34 |
| 5,218,103 | 6/1993 | Caruthers et al. | 536/25.33 |

FOREIGN PATENT DOCUMENTS

WO 95/26972  10/1995  WIPO.

OTHER PUBLICATIONS

Bogachev et al. (1986), 'Phosphorothioate Analogues of Nucleic Acids. Synthesis of 5'–Phosphorothioate Analogues of Oligodeoxyribonucleotides with the Aid of Zwitterionic Monomers.' *Bioorg. Khim.* 12:133.

Bardos et al. (1992), 'Structure–Activity Relationships and Mode of Action of 5–Mercapto–Substituted Oligo–and Polynucleotides as Antitemplates Inhibiting Replication of Human Immunodeficiency Virus Type 1.' *Antimicrobial Agents and Chemotherapy* 36(1):108–114.

Beaton et al. 'Synthesis of oligonucleotide phosphorodithioates.' *Oligonucleotides and Analogues* (Oxford Univ. Press, 1991) Ch. 5, pp. 109–135.

Brill et al. (1989), 'Synthesis of Oligodeoxynucleoside Phosphorodithioates via Thioamidites.' *J. Amer. Chem. Soc.* 111:2321–2322.

Breaker et al. (1990), 'Polynucleotide phosphorylase forms polymers from an ADP analog in which the 5' oxygen is replaced by a methylene group.' *Nucl. Acids Res.* 18(10):3085–3086.

Chladek et al. (1972), 'Nucleophilic Reactions of Some Nucleoside Phosphorothioates.' *J. Amer. Chem. Soc.* 94(6):2079–2085.

Cook (1970), 'Nucleoside S–Alkyl Phosphorothioates. IV.$^1$Synthesis of Nucleoside Phosphorothioate Monesters.' *J. Am. Chem. Soc.* 92:190.

Cosstick et al. (1988), 'Synthesis and Phosphorus–Sulphur Bond Cleavage of 3'–Thiothymidylyl(3'–5')thymidine.' *J. Chem. Soc., Chem. Commun.* 992–993.

Cosstick et al. (1989), 'Solid Phase Synthesis of Oligonucleotides Containing 3'–Thiothymidine.' *Tetrahedron Lett.* 30:4693–4696.

Garegg et al. (1986), 'Nucleoside Hydrogenphosphonates in Oligonucleotide Synthesis.' *Chemica Scripta* 26:59–62.

Heinemann et al. (1991), 'Effect of a single 3'–methylene phosphonate linkage on the conformation of an A–DNA octamer double helix.' *Nucl Acids Res.* 19(3):427–433.

Kawai et al. (1992) 'Synthesis of the thymidine building blocks for a nonhydrolyzable DNA analogue.' *Can. J. Chem.* 70:1573–1580.

Kresse et al. (1975), 'The use of S–2–cyanoethyl phosphorotioate in the preparation of oligo 5'–deoxy–5'–thiothymidylates.' *Nucl. Acids Res.* 2(1):1–9.

Lebedev et al. (1990), 'Stereospecific Coupling Reaction for Internucleotide Methyl Phosphonothioate Linkage.' *Tetrahedron Lett.* 31:855.

Mag et al. (1991), 'Synthesis and selective cleavage of an oligodeoxynucleotide containing a bridged internucleotide 5'–phosphorothioate linkage.' *Nucl. Acids Res.* 19(7):1437–1441.

Michelson (1962), 'Polynucleotides. Part IV, Synthesis of Oligonucleotide Analgues Substituted in the Sugar Portion.' *J. Chem. Soc.* pp. 979–982.

Rybakov et al. (1981), 'Some substrate properties of analogues of oligothymidylates with p–s–C $^5$bonds.' *Nucl. Acids. Res.* 9(1):189–201.

Sproat et al. (1987), 'The synthesis of protected 5'–mercapto–2', 5'–dideoxyribonucleoside–3'–O–phosphoramidities; uses of 5'–mercapto–oligodeoxyribonucleotides.' *Nucl. Acids. Res.* 15(12):4837–4848.

Sund et al. (1989), 'Intra–and Intermolecular Nucleophilic Phosphorus—Sulfur Bond Cleavage. The Reaction of Fluoride Ion with O–Aryl–O,S–Dialkylphosphorothioates, & the Degradation of Phosphorothioate Linkage in di–Ribonucleotides by the Vicinal 2'–Hydroxyl Group.' *J. Tetrahedron* 45:7523.

Vyle et al. (1992) 'Sequence–and Strand–Specific Cleavage in Oligodeoxyribonucleotides and DNA Containing 3'Thiothymidine.' *Biochem.* 31:3012–3018.

Vyle et al. (1992) 'New Methods for the Synthesis of 3'–Phosphorothiolate Internucleoside Linkages.' *Tetrahedron Lett.* 33:3017–3020.

Wada et al. (1990) 'A Facile Conversion of Dialkyl Phosphonates to Dialkyl Phosphorodithioates.' *Tetrahedron Lett.* 31(51):7461–7462.

Reist et al. J. Org. Chem. 29: 554–558, 1964.
Cosstick et al. Nucl. Acids Res. 18:829–835, 1990.

*Primary Examiner*—Gary L. Kunz
*Attorney, Agent, or Firm*—Joan D. Eggert; Ron K. Levy; Steven M. Odre

[57] ABSTRACT

The present invention provides nuclease resistant 5'-dithio-modified oligonucleotides that are useful in nucleic acid therapeutics and diagnostics. The novel modified oligonucleotides have at least one 5'-dithioate linkage, wherein both the oxygen atom at the 5'-position (5'-bridging oxygen) and at least one of the non-bridging oxygen atoms of a naturally occurring phosphodiester linkage are independently replaced with a single sulfur atom. The invention also provides a polymer-supported method for making 5'-dithio-modified and 5'-thio-modified oligonucleotides as well as novel monomeric nucleoside and nucleotide intermediates useful in the synthetic method.

7 Claims, 10 Drawing Sheets or iPr2N - P ( 2 - cyanoethoxy ) - Cl, DIPEA (1)

B = T, G ( nibu ), C ( nbz )

R = iPr or pyrrolidino

PROCESS FOR PREPARING 5-DITHIO-MODIFIED OLIGONUCLEOTIDES

FIELD OF THE INVENTION

This invention relates to the field of therapeutics, and in particular the field of nucleic acid therapeutics.

BACKGROUND

Traditional approaches in drug development have focused on the use of therapeutic agents capable of interacting directly with proteins involved in disease states or other states of unhealth. Drugs borne of this tradition include, for example, synthetic hormones (to simulate the function of protein-based hormones desirably present in the body), antibiotics (which attack foreign proteins, namely those of microorganisms) and vitamins (which provide the building blocks required by certain proteins to perform their ordinary function in the body), in addition to many others. More recently, therapeutic agents in the form of oligonucleotides have been designed to indirectly regulate, control, or otherwise impact protein function by altering at the genetic level the blueprint or machinery that controls synthesis of all proteins. Because each gene contains the information necessary to produce many copies of a particular protein, each of these nucleic acid therapeutic agents can affect a greater number of protein molecules through its indirect interaction than can a traditional macromolecular drug that relies on direct interaction with the targeted protein.

Nucleic acid therapeutic compounds may act in a number of different ways, but will most commonly fall into either one of two categories. The first category includes oligonucleotides that simulate or potentiate in some way a desired genetic effect. The activity stimulated by this type of nucleic acid therapeutic compound is commonly referred to as "gene therapy". The second category of nucleic acid therapeutic compounds includes inhibitory oligonucleotides wherein the nucleic acid therapeutic compound inhibits the production of undesired proteins. Antisense oligonucleotides form a subclass of inhibitory nucleic acid therapeutic compounds, although compounds commonly assigned to this subclass may not always act in a true "antisense" manner. In addition to these two categories of therapeutic oligonucleotides, it should also be noted that it is also possible for nucleic acid therapeutic compounds to interact directly with the target proteins in much the same way as traditional therapeutic drugs.

True antisense interactions involve the hybridization of complementary oligonucleotides (hence, the term "antisense") to their selected nucleic acid target (e.g., viral RNA or other undesired genetic messages) in a sequence specific manner such that the complex thus formed, either alone or in combination with other reagent(s) (e.g., enzymes, such as RNAse) can no longer function as a template for the translation of genetic information into proteins. Other inhibitory oligonucleotides have sequences that are not necessarily complementary to a target sequence, but, like antisense oligonucleotides, have the potential to interfere with the expression (e.g., replication and/or translation) of the undesired genetic material. An antisense oligonucleotide may be designed to interfere with the expression of foreign genes (e.g., viral genes, such as HIV) or with the aberrant expression of endogenous genes (e.g., a normal gene that is aberrantly expressed as a mutated oncogene). These undesired genetic messages are involved in many disease states, including viral infections and carcinomas. Inhibitory oligonucleotides raise the possibility of therapeutic arrest of a disease state at the early replication and expression stage, rather than attacking the resulting protein at a later stage of disease progression as in the manner of traditional drugs.

Oligonucleotides used in gene therapy are designed to provide an oligonucleotide, or synthetic gene, having a desired effect that is otherwise absent or impaired in a patient. Each gene normally present in a human body is responsible for the manufacture of a particular protein that contributes to either the structure or functioning of the body. If this gene is defective or absent, protein synthesis will be faulty or nonexistent, and a deformity or genetic disease will result. Incorporation of nucleic acid therapeutic compounds into the genetic material of a patient's cells can be accomplished through a vehicle, such as a retrovirus, thus enabling production of the needed protein.

Irrespective of whether nucleic acid therapeutic compounds are designed for gene therapy, antisense therapy, or any other situation where it is desired to affect proteins at a genetic or other level, the design of these synthetic oligonucleotides is a key to the level of success that can be achieved. Importantly, these oligonucleotides must ordinarily be modified in a manner that imparts nuclease resistance to the oligonucleotide such that they are capable of surviving in the presence of the various nucleases that are endogenous to a human or animal body. The same holds true for oligonucleotide probes employed in the analysis of serum samples, because the same exogenous nucleases present in the human body that can degrade unmodified therapeutic oligonucleotides are also present in human serum and can degrade unmodified oligonucleotide probes in these samples as well.

Specifically, unmodified (or "wild type") oligonucleotides are susceptible to nuclease degradation at both the 3'- and 5'-positions of the inter-nucleotide bonds that link the individual nucleoside units together in the completed oligonucleotide. Consequently, attempts to impart nuclease resistance to therapeutic oligonucleotides have been directed to modification of this internucleotide linkage, with success having been achieved primarily with respect to modification of the "non-bridging" oxygen atoms in the naturally occurring phosphodiester linkage. (E.g., phosphorothioate-modified oligonucleotides having a single non-bridging oxygen substituted with a sulfur atom (U.S. Pat. No. 3,846,402) and phosphorodithioate-modified oligonucleotides having both non-bridging oxygen atoms substituted with sulfur atoms (U.S. Pat. No. 5,218,103)). It has been observed, however, that phosphorothioate-modified oligonucleotides remain susceptible to nuclease degradation at the 3'-position of the modified internucleotide bonds in some instances, especially by nucleases leaving a 5'-phosphate following cleavage of the internucleotide bond. This is presumably due to the fact that only one of the "non-bridging" oxygen atoms in the phosphodiester bond is modified.

Other attempts to impart nuclease resistance to therapeutic or diagnostic oligonucleotides have been directed to modification of the "bridging" oxygen atoms in the naturally occurring phosphodiester linkage, with some limited success having been achieved. For example, the synthesis of an oligonucleotide containing a single 3'-methylene substitution (i.e., the 3'-bridging oxygen is substituted with a methylene (—$CH_2$—) group) has been reported. Heinemann et al., *Nucleic Acids Res.,* 19, 427–433 (1991). However, synthesis of the nucleoside intermediates required for the reported solution-based phosphotriester method of generating the internucleotide linkage is long and laborious, making the synthesis of multiple 3'-methylene modifications in an oligonucleotide difficult and tedious. Consequently, nuclease stability for oligonucleotides containing the 3'-methylene linkage have only recently been reported.

Modified oligonucleotides containing bridged phosphoramidate linkages (i.e., either the 5'-oxygen or the 3'-oxygen is replaced by an amino (—NH—) group) have been synthesized. Gryaznov et al., *Nucleic Acids Res.,* 20, 3403–3409, (1992) and Mag et al., *Tetrahedron Lett.,* 33, 7323–7326 (1992). Similarly, modified oligonucleotides containing 3'-thio-bridged linkages (3'-bridging oxygen substituted with a sulfur atom) have been synthesized. Cosstick et al., *Nucleic Acids Res.,* 18, 829–834 (1990); Vyle et al., *Biochemistry,* 31, 3012–3018 (1992). Modification of the 3'-oxygen by an amino or sulfur moiety has been found to confer some resistance to nuclease degradation, however, it has been observed that phosphoramidate and 3'-thio-bridged modified oligonucleotides remain susceptible to degradation of the modified internucleotide bond, presumably because a single modification to only one of the "bridging" oxygens is insufficient to confer significant nuclease resistance (i.e., similar to the above-described phosphorothioate modification).

The synthesis of modified oligonucleotides containing a single 5'-thio-bridged substitution (5'-bridging oxygen substituted with a sulfur atom) has also been reported. Mag et al., *Nucleic Acids Research,* 19, 1437–1441 (1991). However, this method is not compatible with the synthesis of modified oligonucleotides having more than a single 5'-thio-bridged linkage, because the deprotection reaction required to complete formation of the desired modified internucleotide bond employs silver or mercury salts to cleave the trityl protecting group from the 5'-thiol moiety. These salts would also necessarily cleave any previously formed P—S bond in the oligonucleotide. Other known solution-phase methods for making modified oligonucleotides containing multiple 5'-thio-bridged modifications are based on phosphodiester technology and are incompatible with automated, polymer-supported synthesis of oligonucleotides. Moreover, the 5'-thio-bridged modification alone would not be expected to impart sufficient nuclease resistance to oligonucleotides for use as a nucleic acid therapeutic, because only one of the "bridging" oxygens is modified.

It would be desirable to have a further dithio-modified oligonucleotide of a length that would be suitable for use as a nucleic acid therapeutic compound or as a diagnostic probe and would have a type of thio-bridged modified linkage that is able to impart nuclease resistance to the modified oligonucleotide.

Therefore, it is an object of the present invention to provide dithio-modified oligonucleotides having a sulfur substitution at the 5'-position of at least one of the internucleotide linkages.

It is a further object of the present invention to provide a polymer-supported method for synthesis of oligonucleotides having a 5'-bridging sulfur substitution of one or more of the internucleotide bonds.

It is a still further object of the present invention to provide novel nucleoside intermediates for use in the synthesis of oligonucleotides having 5'-thio-bridged modification(s).

SUMMARY OF THE INVENTION

The present invention provides nuclease resistant oligonucleotides having at least one internucleotide linkage wherein the bridging oxygen atom at the 5'-position of the internucleotide linkage is replaced by a sulfur atom and at least one of the non-bridging oxygen atoms of the naturally occurring phosphodiester bond is also replaced with a sulfur atom. Also provided are a method and intermediates for making 5'-dithioate and 5'-thioate modified oligonucleotides. The modified oligonucleotides of the present invention can be used in the field of nucleic acid therapeutics, probe diagnostics, or any other application where a nuclease-resistant oligonucleotide is desired or advantageous.

DETAILED DESCRIPTION OF THE INVENTION

Figure 1:
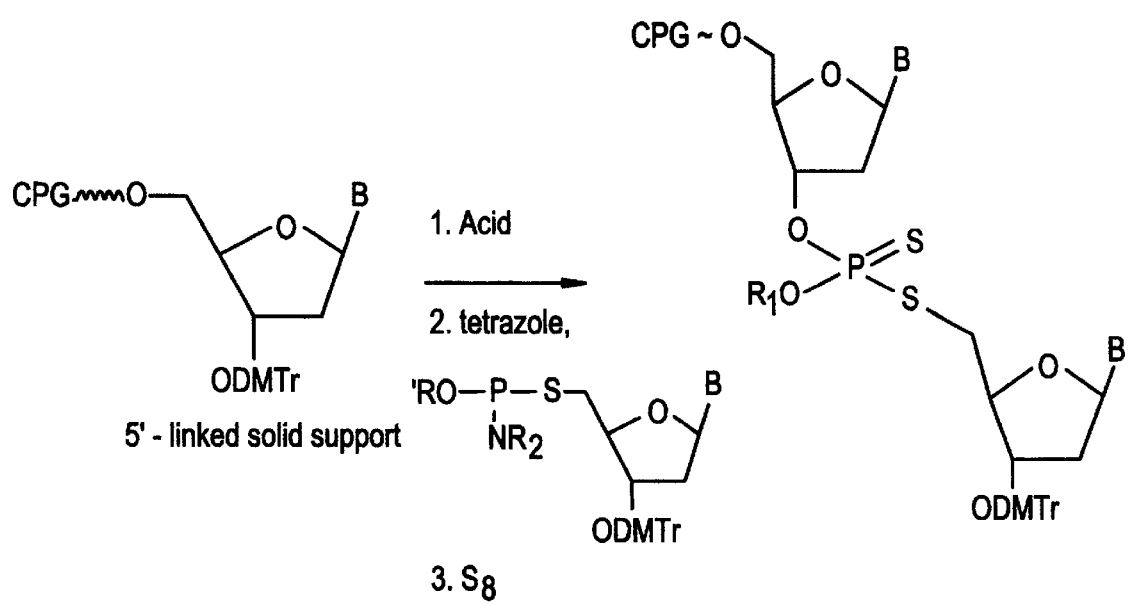
FIG. 1 shows synthesis of a 5'-dithio-modified linkage through the coupling of a 5'-thiophosphoramidite synthon to the 3'-end of a polymer-supported nucleotide.

The present invention provides nuclease resistant 5'-dithio-modified oligonucleotides useful in nucleic acid therapeutics and diagnostics. These novel oligonucleotides contain at least one 5'-dithioate linkage, wherein both the oxygen atom at the 5'-position (5'-bridging oxygen) and at least one of the non-bridging oxygen atoms of a naturally occurring phosphodiester linkage are independently replaced with a single sulfur atom. Also contemplated by the present invention is a method for making 5'-dithio-modified and 5'-thio-modified oligonucleotides. Novel monomeric nucleoside and nucleotide intermediates useful in making these modified oligonucleotides by polymer-supported synthesis are also contemplated within the scope of the present invention.

It is worth noting that the substitution of both a 5'-bridging sulfur atom and at least one non-bridging sulfur atom for the corresponding oxygen atoms in a phosphodiester bond render the resulting modified 5'-dithioate linkage chiral, leading to a mixture of isomers of this particular linkage. However, where both of the non-bridging oxygen atoms of the phosphodiester bond are replaced with sulfur atoms, the 5'-dithioate linkage of the present invention retains the same achiral character as naturally occurring phosphodiester internucleotide bonds. Irrespective of the chirality of the particular form of 5'-dithio-modified linkage, the 5'-dithioate linkage of the present invention is a conservative modification that allows the modified oligonucleotide to retain a significant level of binding affinity and sequence specificity to target DNA or mRNA. This is an important feature, because these characteristics are frequently exploited in the various contemplated applications for the 5'-dithioate oligonucleotide of the present invention.

For example, in the case of both traditional antisense approaches to nucleic acid therapeutics and diagnostic probe assays, it will be necessary for the modified oligonucleotide to hybridize to its intended therapeutic or diagnostic target. (E.g., hybridization of the modified oligonucleotide to the mRNA of a virus or the gene associated with a disease state in the case of traditional antisense therapeutics.) Thus, stability of the duplex formed when the modified oligonucleotide hybridizes to its corresponding target is important (in addition to the nuclease stability imparted by the 5'-dithioate modification).

In order to aid in the understanding of the present invention, the following terms, as used herein, have the definitions designated below.

"Oligonucleotide" refers to a polymer of at least two nucleoside units, wherein each of the individual nucleoside units is covalently linked to at least one other nucleoside unit through a single phosphorus moiety. In the case of naturally occurring oligonucleotides, the covalent linkage between nucleoside units is a phosphodiester bond. Nevertheless, the term "oligonucleotide", as used herein, includes oligonucleotides that are modified (as compared to naturally occurring oligonucleotides) with respect to any one or more of the following: (1) the phosphodiester bond between nucleoside units; (2) the individual nucleoside units themselves; and/or (3) the ribose, or sugar, moiety of the nucleoside units.

Unless otherwise specified, the term "base" or "nucleobase" refers to a purine or pyrimidine, such as adenine, guanine, cytosine, thymine and uracil as well as modified forms of these bases, such as 5-methylcytosine and 5-propynyl pyrimidines.

"Nucleoside" refers to an individual monomeric nucleoside unit consisting of a base covalently bonded to the 1'-position of a 5-carbon sugar. The 5-carbon sugar will typically be a naturally occurring sugar such as deoxyribose, ribose or arabinose, but can be any 5-carbon sugar or modified form thereof, including but not limited to, 2'-fluoro-2'-deoxyribose or even carbocyclic sugars where a carbon function is substituted for the oxygen atom in the sugar ring (i.e., 6-carbon analog). Typically, the base will be linked to the sugar moiety at conventional positions, such as N9 of adenine, guanine and other purines or N1 of cytosine, thymine, uracil and other pyrimidines.

"Nucleotide" refers to a monomeric nucleoside unit further having a phosphorus moiety covalently bonded to the sugar moiety of the nucleoside at either the 3'- or 5'-position of the sugar.

A "modified internucleotide linkage" refers to a modification of the phosphodiester bond joining individual nucleoside units in naturally occurring oligonucleotides.

The term "modified oligonucleotide" specifically refers to an oligonucleotide having at least one modified internucleotide linkage.

The term "partially modified oligonucleotide" means a modified oligonucleotide wherein at least one but fewer than all internucleotide linkages are modified.

The term "fully modified oligonucleotide" means a modified oligonucleotide wherein all of the internucleotide linkages are modified.

The term "5'-thioate" internucleotide linkage or "5'-thioate-modified" linkage means an internucleotide linkage wherein the oxygen atom at the 5'-position is replaced with a sulfur atom.

The term "5'-dithioate" internucleotide linkage or "5'-dithio-modified" linkage means an internucleotide linkage wherein the oxygen atom at the 5'-position and at least one of the non-bridging oxygen atoms of a phosphodiester internucleotide linkage are each independently replaced by a single sulfur atom. Thus, a "5'-dithioate linkage", as defined herein, includes a 5'-trithioate linkage; i.e., where both of the non-bridging oxygen atoms in the phosphodiester linkage are replaced with sulfur atoms.

The term "5'-dithio-modified oligonucleotide" or 5'-dithioate oligonucleotide" refers to an oligonucleotide having at least one 5'-dithioate linkage.

"Target sequence" refers to the nucleotide sequence to which an oligonucleotide or a modified oligonucleotide is designed to hybridize. In the case of inhibitory oligonucleotides, the "target sequence" may be, but is not necessarily limited to, a naturally occurring messenger RNA coding for a viral protein, cancer related protein or other proteins involved in disease states.

Specifically, the 5'-dithio-modified oligonucleotides of the present invention have at least one 5'-dithioate internucleotide linkage as shown below.

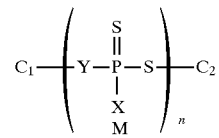

In this structure, C1 and C2 represent the 3'-position and 5'-position, respectively, of the nucleoside units which are joined together in the oligonucleotide through the 5'-dithio-modified internucleotide linkage of the present invention.

This 5'-dithioate modified internucleotide linkage can be more fully described with reference to the following structure, which shows the individual nucleoside units surrounding this particular linkage in greater detail.

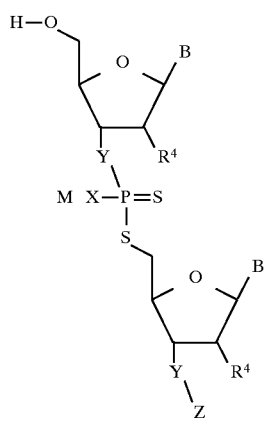

With reference to this oligonucleotide structure, B is a purine or pyrimidine base, typically adenine, guanine, cytosine or thymine (in the case of DNA) or uracil (in the case of RNA). Z is either a hydrogen (—H—) atom, where B is a terminal base of the oligonucleotide, or the phosphorus atom in the next internucleotide linkage of the oligonucleotide. $R^4$ is typically a hydrogen (—H—) atom (in the case of DNA) or a hydroxyl (—OH—) moiety (in the case of RNA, or in the case of an oligonucleotide having arabinose units in the backbone), but can be other atoms or moieties, such as fluorine (—F—) where other 5-carbon sugars are used in the backbone of the oligonucleotide. Y is typically an oxygen atom (—O—), but can be other atoms or moieties, such as divalent substituents (e.g., sulfur (—S—), methylene (—CH$_2$—), or substituted methine (—CHR—), depending on: (1) whether the nucleoside used as a starting material has a 3'-modification; and, (2) the method used for oligonucleotide synthesis.

Typically, X is either oxygen (in the case of the more typical 5'-dithioate linkage of the present invention, having a sulfur substitution for only one of the non-bridging oxygen atoms) or a sulfur atom (in the case of the 5'-trithioate form of the 5'-dithioate linkage, as defined herein). X can also be an alkyl group (e.g., methyl or substituted alkyl chain), depending on the substitution, if any, made at phosphorus atom in the intermediates used for synthesis of the completed oligonucleotide. M is typically a cation, such as sodium, potassium or triethylammonium. However, M can also be an alkyl (methyl) or a substituted alkyl group (such as 2-cyanoethyl) in the case of a modified linkage prior to removal of the protective group, as described below.

The present invention further provides rapid and efficient polymer-supported methods for making oligonucleotides containing the above-described 5'-dithio-modified linkage. These methods are also applicable to the synthesis of 5'-thioate linkages and can be adapted to make modified oligonucleotides of lengths comparable to those of unmodified oligonucleotides made by traditional polymer-supported techniques. This is important, because oligonucleotides of approximately 10 to 12 bases or longer are typically required for use as sequence specific probes for simple genomes such as E. coli. The upper limit of approximately 60 nucleotide bases is established for isothermal processes, because the melting temperatures ($T_m$) of longer oligonucleotide products converge upon the same value at or about this point. Antisense oligonucleotides, on the other hand, must be effective at physiological temperatures, and are typically about 15 to 25 nucleotides long. Generally, longer antisense oligonucleotides within this range are desirable, because they have a lower probability of occurring by chance in large genomes. For example, a 17-mer oligonucleotide should be unique to a mammalian genome. On the other hand, if an antisense oligonucleotide is too long (i.e., substantially longer than 25 nucleotides), it may hybridize nonspecifically to other non-target sequences. This type of nonspecific hybridization is unavoidable, because the physiological body temperature of a patient cannot be adjusted to increase stringency.

The 5'-dithioate oligonucleotides of the present invention can be synthesized in any one of a number of ways that will become apparent to one of ordinary skill in the art following the teachings of the present invention. Generally, there are two preferred methods of synthesis, both of which employ the use of novel monomeric nucleoside units en route to the desired modified oligonucleotide product. These methods may employ unconventional (5'→3') synthesis (in the case of the first, namely phosphoramidite, method) or conventional (3'→5') direction of synthesis (in the case of the second, namely H-phosphonate, method, which employs novel nucleoside 3'-alkylhydrogenphosphonate or nucleoside 3'-alkylthiophosphonate intermediates).

A first preferred method of making the 5'-dithio-modified oligonucleotides of the present invention utilizes traditional phosphoramidite technology, but proceeds in the less commonly used 5'→3' direction of synthesis. The 5'-thiophosphoramidite synthon used in the automated phosphoramidite method is shown below.

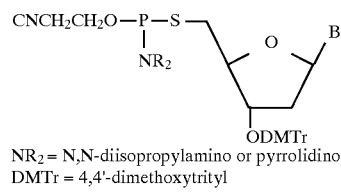

$NR_2$ = N,N-diisopropylamino or pyrrolidino
DMTr = 4,4'-dimethoxytrityl

This thiophosphoramidite synthon incorporates a 5'-bridging sulfur atom into the desired oligonucleotide product via the coupling of this monomeric unit to a growing polymer-supported oligonucleotide chain, as shown in FIG. 1. The coupling reaction can be used to generate partially modified 5'-dithioate oligonucleotides (containing both 5'-dithio-modified linkages and unmodified phosphodiester linkages), in addition to fully 5'-dithio-modifed oligonucleotides, by simply using commercially available 5'-phosphoramidites for coupling conventional nucleotide synthons to the growing oligonucleotide chain where the unmodified linkages are desired.

Ordinarily, polymer-supported synthesis of oligonucleotides is initiated through a nucleoside that has been attached to a solid support as a starting point. Most commonly, the first nucleoside is attached at the 3'-oxygen of the nucleoside, and the synthesis occurs in a 3'→5' direction using 3'-phosphoramidites. However, according to the thiophosphoramidite method of the present invention, synthesis proceeds in the less commonly used 5'→3' direction. Nonetheless, commercially available 5'-linked solid supports can be used in the initial coupling reaction. As noted above, the 5'-thiophosphoramidite synthons can be interchanged as desired with readily available 5'-phosphoramidite synthons during polymer-supported synthesis of the desired oligonucleotide end-product.

Figure 2:
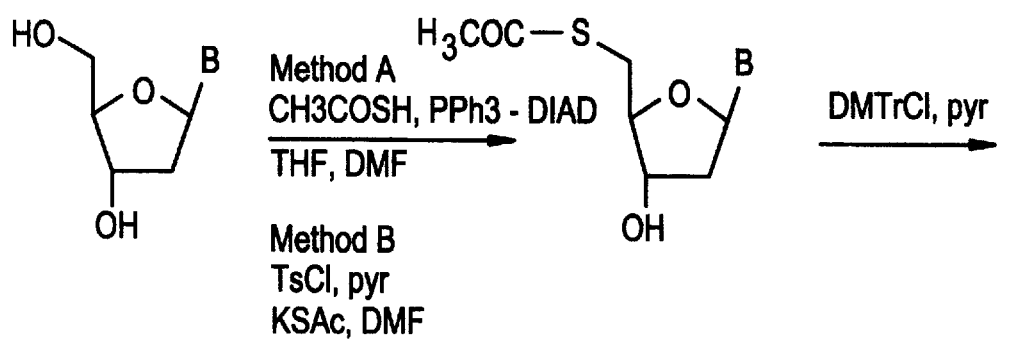
FIG. 2 shows the synthesis of 5'-thiophosphoramidite synthons used to generate the 5'-dithio-modified internucleotide linkage of the present invention through polymer-supported phosphoramidite chemistry in an unconventional 5'→3' direction.
Figure 2:
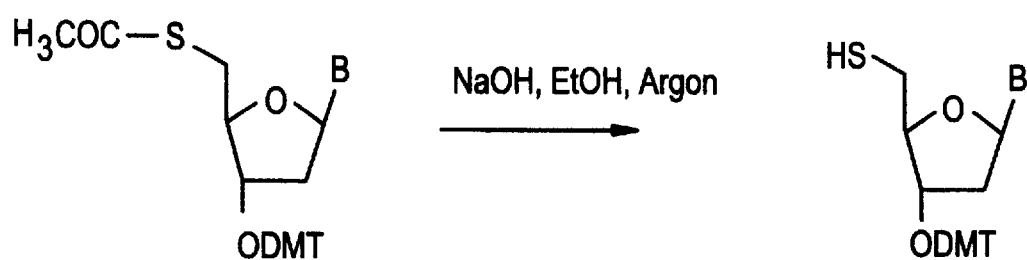
Figure 2:
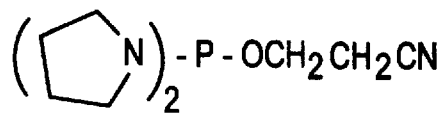
Figure 2:
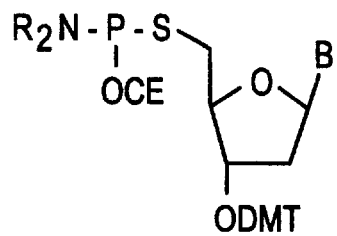

Synthesis of the 5'-thiophosphoramidite synthon used in the phosphoramidite method of the present invention is preferably accomplished according to the synthetic scheme outlined in FIG. 2. This scheme requires that a monomeric the less (acetyl)-nucleoside intermediate be obtained in the first instance. This monomeric nucleoside intermediate is preferably made according to one of two methods.

The first method is generally more preferred, because it employs a single step. In this method, a commercially available nucleoside is reacted with thiolacetic acid in a regio-selective Mitsunobu coupling reaction according to methods known in the art, whereby the 5'-hydroxyl group of the nucleoside, a primary alcohol, reacts selectively with the thiolacetic acid in the presence of the secondary 3'-hydroxyl group which does not participate in the coupling reaction. (See Mitsunobu, *Org. Synthesis*, 1–28 (1981); Kawai, et al. *Can. J. Chem.*, 70, 1573–1580 (1992).) The reaction of the 2'-deoxynucleoside with thiolacetic acid takes place in the presence of triphenylphosphine and diisopropylazodicarboxylate and, at 0° C., produces moderate to good yields of the 2',5'-dideoxy-5'-S-(acetyl)-nucleoside without requiring prior protection of the secondary 3'-hydroxyl functionality, which would, of course, increase the number of synthetic steps.

Alternatively, the 2',5'-dideoxy-5'-S-(acetyl)-nucleoside can also be made according to a two-step procedure, whereby the 5'-hydroxyl group of a 2'-deoxynucleoside is first converted to the tosylate, with the intermediate tosylate subsequently being displaced by reaction with potassium thiolacetate. (See, Reist et al., *J. Org. Chem.* 29, 554–558 (1964)).

The 3'-alcohol of the 2',5'-dideoxy-5'-S-(acetyl)-nucleoside intermediate (which results from either of the above two methods) is then protected with 4,4'-dimethoxytrityl chloride, after which the acetyl group is removed by careful treatment with base, and the resulting 2',5'-dideoxy-5'-mercapto nucleoside is phosphitylated to yield the 5'-thiophosphoramidite synthon.

Simple modification of the cycles replacing the conventional iodine oxidation step with a sulfur oxidation reaction yields the second (i.e., non-bridging) sulfur atom in the 5'-dithioate linkage of the present invention.

The thiophosphoramidite method can be employed to synthesize 5'-dithio-modified oligonucleotides containing substitutions at other positions of the internucleotide linkage by using different phosphines in the phosphitylation step from the same 2, 5'-dideoxy-5'-S-nucleoside in combination with diverse oxidation protocols during solid phase synthesis.

A second preferred method for making the 5'-dithioate modified oligonucleotides of the present invention proceeds in the more commonly used 3'→5' direction, but reverses the polarity of the coupling reactions in conventional polymer-supported oligonucleotide synthesis in order to form the desired P—S internucleotide linkage. According to conventional phosphoramidite or H-phosphonate oligonucleotide synthesis technologies, a hydroxyl group acts as a nucleophile, with a phosphorus intermediate acting as the electrophile in the coupling reaction between the appropriate nucleotide synthon and the terminal base of a polymer-supported oligonucleotide chain. Specifically, a hydroxyl group acts as the nucleophile, while the phosphorus intermediate acts as the electrophile in either: (1) the tetrazole-catalyzed reaction in the case of phosphoramidite technology; or, (2) condensation reaction in the case of conventional H-phosphonate chemistry.

Most commonly, conventional phosphoramidite chemistry is employed whereby the nucleophilic hydroxyl group in the coupling reaction is the 5'-hydroxyl group of the 3'-polymer-supported nucleotide base and the monomeric synthon is a 3'-phosphoramidite nucleoside. In the less commonly used H-phosphonate chemistry, the nucleophilic hydroxyl group is still the 5'-hydroxyl of the 3'-polymer-supported nucleotide base, but the monomeric synthon is a nucleoside 3'-H-phosphonate salt. In the latter case, the 3'-H-phosphonate salt requires activation by the use of a condensation agent (e.g., pivaloyl chloride, pyridine) before it can react with the 5'-hydroxyl nucleophile.

There are, of course, other known methods for synthesizing internucleotide linkages, although these other methods are not commonly used in automated solid-phase synthesis of oligonucleotides. Nevertheless, these other methods similarly employ the phosphorus atom of the internucleotide linkage as the electrophile in the desired reaction. For example, previous use of alkyl nucleoside 3'-hydrogenphosphonates in oligonucleotide synthesis strategies has involved activation of these intermediates by chlorination at the phosphorus atom so that the phosphorus atom still acts as the electrophile in reaction with the nucleophilic 5'-hydroxyl group of the nucleoside synthon.

In contrast to these known methods, a novel base-catalyzed reaction is employed according to the present invention to accommodate the coupling reaction between the polymer-supported terminal nucleoside unit of the growing oligonucleotide chain and a novel 3'-methylhydrogen-thiophosphonate nucleoside synthon which is employed in this synthetic method. The novel nucleoside 3'-methylthiophosphonate synthon is shown below.

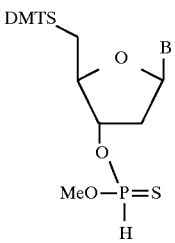

In accordance with the novel base-catalyzed reaction of the present invention, the base effects abstraction of the hydrogen atom from the 3'-methylthiophosphonate synthon, which allows the phosphorus atom to act as a nucleophile. The now nucleophilic (activated) phosphorus atom of the synthon reacts with the 5'-S-sulfide, or 5'-disulfide, of the 3'-polymer-supported nucleotide base, which acts the electrophile in this reaction. The base-catalyzed coupling reaction described herein is surprisingly fast in solution, in contrast to the previously known Michaelis-Arbuzov reaction of phosphites with asymmetrical disulfides. (Vyle et al., *Tetrahedron Letters*, 33, 3017–3020 (1992) (16 hours at room temperature needed to drive reaction to completion).)

In the second preferred (H-thiophosphonate) synthetic method of the present invention, the monomeric subunit, or synthon, employed in the coupling reactions is a nucleoside 3'-alkylhydrogen-phosphonate (either the novel thio-(—S—) of the present invention or an oxy-(—O—) function for 5'-thio-bridged linkages). Under base catalysis, these monomeric alkylhydrogen-phosphonate synthons react with a reactive asymmetrical disulfide of the polymer-supported terminal nucleoside unit of the oligonucleotide chain being synthesized.

The novel nucleoside 3'-methylhydrogen-phosphonate synthons of the present invention can be readily made by reacting a water ($H_2O$)/tetrazole or hydrogen sulfide ($H_2S$)

/tetrazole reagent with a commercially available methyl (—Me—) phosphoramidite to generate the monomeric synthon for coupling to the growing oligonucleotide chain during polymer-supported synthesis. In the case of a simple 5'-thio-bridged internucleotide linkage, hydrolysis of a nucleoside 3'-methylphosphoramidite with water in the presence of tetrazole results in the corresponding 3'-methylphosphonate. (See, Garegg et al., *Chemica Scripta*, 26, 59–62 (1986), and Gryaznov, et al., *Nucleic Acids Res.*, 20, 3403–3409 (1992), for description of an analogous procedure.) Similarly, for the 5'-dithioate modified linkage, hydrosulfenolysis of a nucleoside 3'-methylphosphoramidite in the presence of tetrazole yields the corresponding 3'-methylthiophosphonate, as shown below.

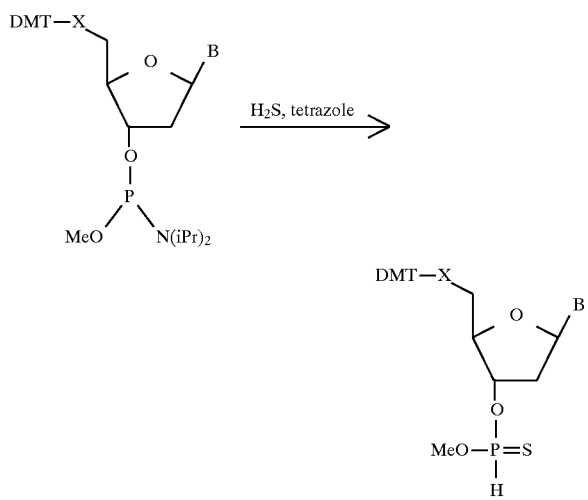

As in the case of synthesis according to the previously described thiophosphoramidite method, polymer-supported synthesis of modified oligonucleotides by the H-thiophosphonate method is initiated through a nucleoside that has been attached to a solid support as a starting point. Because the H-thiophosphonate method proceeds according to an unconventional base-catalyzed chemistry, where sulfur replaces oxygen at the 5'-position of the nucleoside, commercially available 3'-linked solid supports are not applicable, and the first nucleoside unit (i.e., a 2',5'-deoxy-5'-S-(4,4'-dimethoxytrityl)-nucleoside) must be attached to a suitable solid support before internucleotide linkages can be formed.

Figure 3:
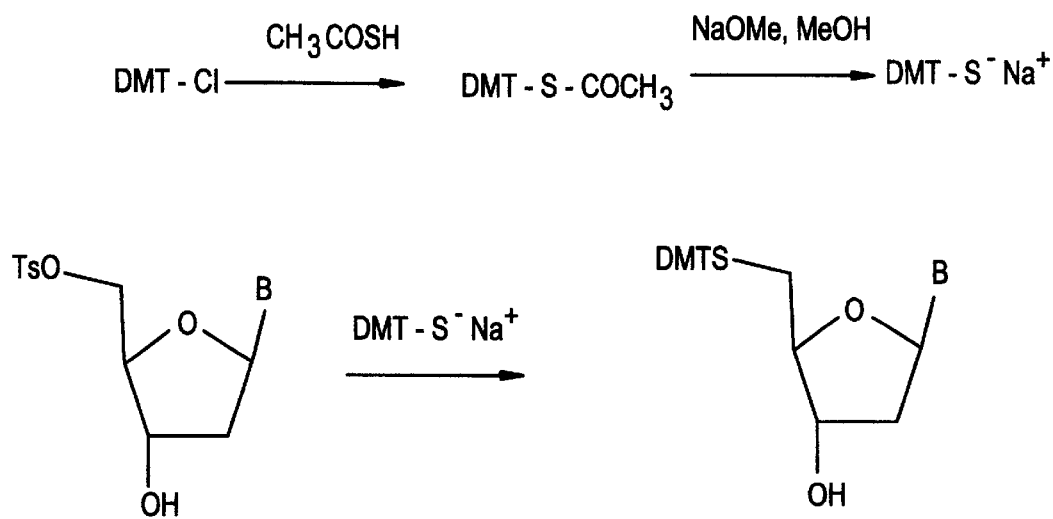
FIG. 3 is a diagram of the synthesis of a 2',5'-dideoxy-5'-S-(4,4'-dimethoxytrityl) nucleoside intermediate used in the H-thiophosphonate method of making the 5'-dithioate linkage of the present invention.

The synthetic scheme for achieving the 2',5'-dideoxy-5'-S-(4,4'-dimethoxytrityl) nucleoside is diagrammed in FIG. 3. Initially, 4,4'-dimethoxytrityl chloride is reacted with thiolacetic acid to generate a 4,4'-dimethoxytrityl thiolacetate, which is then treated with base (sodium methoxide) to produce a 4,4'-dimethoxytrityl sodium thiolate salt. The resulting sodium thiolate is then reacted with the 5'-O-(tosylate) of 2'-deoxynucleosides, which have been prepared according to methods known in the art. (See, e.g., Reist, et al. *J. Org. Chem.*, 29, 554–558 (1964).) This reaction, also shown in FIG. 2, yields the 2',5'-dideoxy-5'-S-(4,4'-dimethoxytrityl) nucleoside intermediates needed for the H-thiophosphonate method of the present invention.

Figure 4:
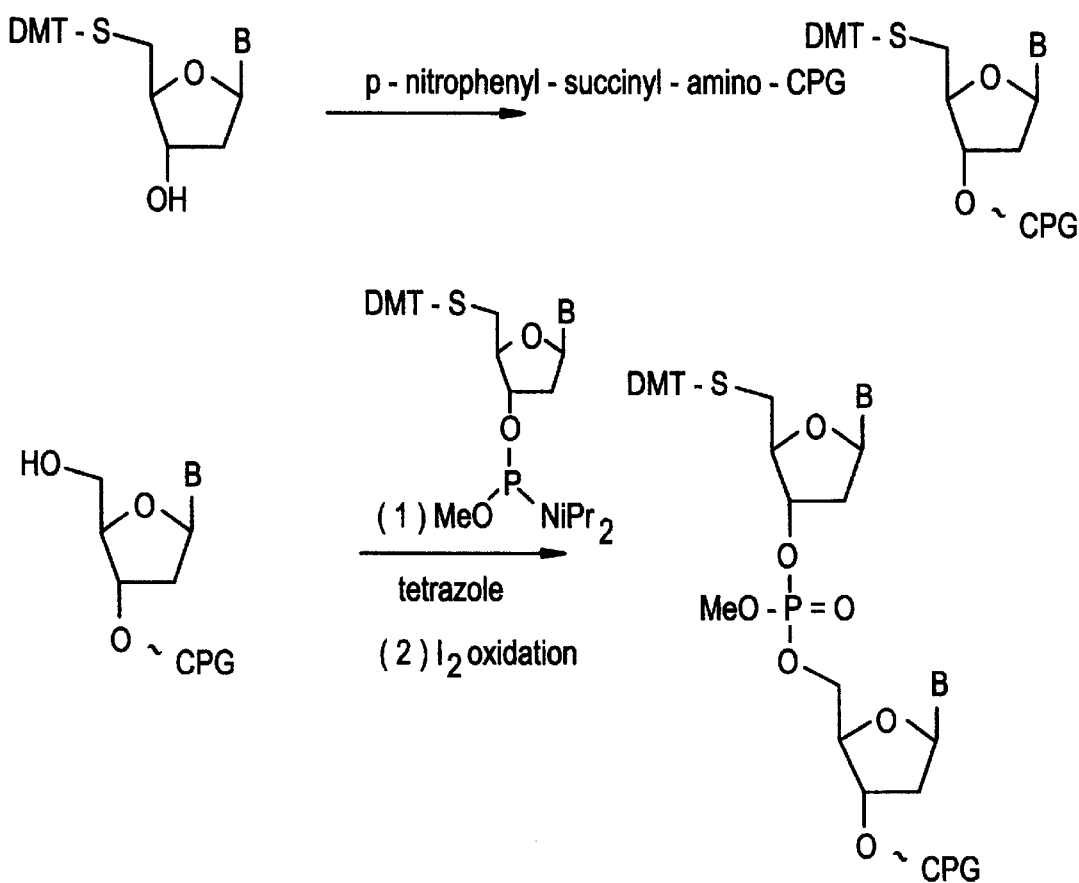
FIG. 4 shows alternate methods for achieving attachment of a protected 2',5'-dideoxy-5'-S-(4,4'-dimethoxytrityl) nucleoside to a solid support.

Attachment of the 5'-protected thiol nucleoside to the solid support can be accomplished through derivatization of the unprotected 3'-position according to established synthetic methods. A preferred solid support is controlled pore glass, but it will be appreciated that other solid supports are known in the art and will be suitable for synthesis according to the method of the present invention. Attachment of the first nucleoside to the solid support may be achieved using conventional succinyl or sarcosinyl linkers, but is not limited to reactions employing these reagents. As an example, derivatization of the 3'-hydroxyl with succinic anhydride, followed by activation with dicyclohexyl carbodiimide (DCC)-p-nitrophenol, and then reaction with amino derivatized CPG can be done, as well as reaction of the 3'-hydroxyl with activated resins as shown in FIG. 4. Alternatively, commercially available CPG supports containing 3'-anchored nucleosides can be used, provided the 3'-phosphoramidite of the 2',5'-dideoxy-5'-S-(4,4'-dimethoxytrityl) nucleoside is used as further shown in FIG. 4. The resulting suitably derivatized solid-support is then used to initiate the 3'→5' solid-phase synthesis of 5'-dithio-modified oligonucleotides using conventional DNA/RNA synthesizers and the nucleoside 3'-methylhydrogenthiophosphonate synthons described herein.

For polymer-supported oligonucleotide synthesis of the 5'-dithioate linkage according to the H-thiophosphonate method of the present invention, conversion of a 2',5'-dideoxy-5'-S-(4,4'-dimethoxytrityl) nucleoside function to the corresponding reactive disulfide is a novel and critical step. Methods for generating these reactive disulfides in situ according to solid phase synthetic methods are further described below.

By way of background, it is worth noting initially that the an accepted method for removal of an S-t-butyl thioether protective group from a thiol is by treatment with o-nitrophenylsulfenyl chloride to form an intermediate asymmetrical disulfide, which can then be reduced with sodium borohydride to yield the free thiol moiety. (See, *Greene's Protective Groups in Organic Chemistry*, 2nd edition, 289, Wiley (1991).) In the case of S-triphenylmethyl thioether (also known as a trityl protecting group), the use of acids in the presence of metals such as silver or mercury is required to effect removal of this protecting group, because acids alone do not completely dissociate the sulfur-carbon bond. However, the use of these metals is not compatible with solid phase synthesis of consecutive 5'-dithioate linkages because the metals will cleave any P—S bonds that have been previously formed in the growing oligonucleotide chain. Because 4,4'-dimethoxytrityl protective groups are more acid labile than trityl groups, it is preferred to protect the thiol with the more labile 4,4'-dimethoxytrityl function so that mild acid treatment, in combination with the presence of an arylsulfenyl chloride, can successfully promote the formation of an intermediate asymmetrical disulfide.

Thus, according to the present invention, removal of a 4,4'-dimethoxytrityl group from a 5'-thiol moiety can be carried out under mild acid conditions, provided the acid treatment is performed in the presence of 2,4-dinitrobenzenesulfenylchloride to generate an asymmetrical 2,4-dinitrobenzenesulfenyldisulfide. The formation of an asymmetrical disulfide can also be accomplished by addition to the acid solution other thiols or disulfides, for example, p-nitrothiophenol or 2,2'-dithiobis(5-nitropyridine).

It is important to note that without any addition of thiol or disulfide reagents, partial removal of the 4,4'-dimethoxytrityl group can be achieved under mild acid conditions, and the resulting postulated symmetrical disulfide can react in the subsequent coupling reaction with H-phosphonate synthons. However, the reaction of the symmetrical disulfide with the H-thiophosphonate or H-phosphonate synthons will result in reduced yields of the modified internucleotide linkage, due to the formation of a nucleoside 5'-thiol as a side product from this reaction.

Consequently, the formation of a symmetrical disulfide is neither preferred nor desired.

Figure 5:
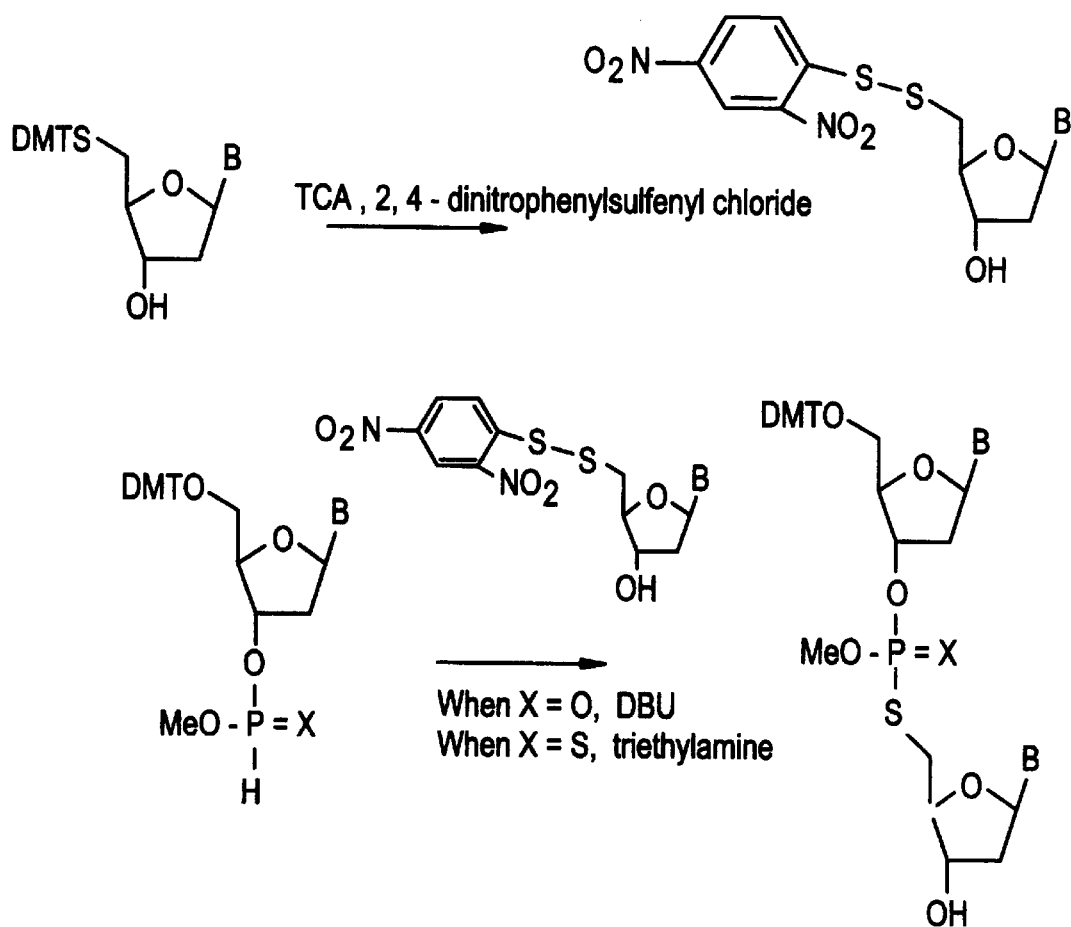
FIG. 5 shows the removal of a 4,4'-dimethoxytrityl protecting group from a 5'-thiol moiety (dimethoxytritylthiothymidine) under mild acid conditions in the presence of arylsulfenylchloride to generate an asymmetrical 2,4-dinitrosulfenyl-disulfide (dinitrobenzenesulfenyl-thiothymidine). Also shown is the further coupling of the resulting asymmetrical 2,4-dinitrosulfenyl-disulfide with two different types of H-methylphosphonate synthons to generate either 5'-thio-bridged or 5'-dithioate modified dimers.

For solution-phase synthesis, rapid conversion of, e.g., 2',5'-dideoxy-5'-dimethoxytritylthiothymidine to the corresponding dinitrobenzenesulfenyl-thiothymidine can be achieved in a single step, with subsequent isolation of the resulting asymmetrical disulfide by chromatographic purification. Solution-phase synthesis of the dinitrobenzenesulfenyl-thiothymidine dimer is shown in FIG. 5. Reaction of the dinitrobenzenesulfenyl-thiothymidine intermediate with two different H-phosphonate synthons, as shown in FIG. 5, results in the production of modified dimeric oligonucleotides when carried out in pyridine/benzene solvent. More specifically, in the case of a simple 5'-thio-modified internucleotide linkage, the use of DBU (1,8-diazabicyclo[5.4.0]undec-7-ene) as a catalyst in pyridine/benzene results in the clean formation of 5'-thio-modified dimers in solution. However, where the more complex 5'-dithioate linkage of the present invention is desired, it is necessary to use the more reactive H-thiophosphonate synthon, and, as a consequence, triethylamine is preferred for use as the base to attain clean and rapid conversion to the desired dimeric oligonucleotides.

Conditions for the novel solid phase synthesis of 5'-thioate and 5'-dithioate linkages according to the H-thiophosphonate method of the present invention generally involve two steps. (See FIG. 6). Beginning with a 2',5'-dideoxy-5'-S-(4,4'-dimethoxytrityl)nucleoside attached to the solid support as a starting point, the first step is a combined deblock/activation step, achieved by using a solution of 2.5% trichloroacetic acid (TCA) containing either dinitrobenzenesulfenyl chloride, p-nitrothiophenol, or 2,2'-dithiobis(5-nitropyridine). This reaction removes the dimethoxytrityl protecting group and converts the unmasked thiol to a disulfide by sulfenylation of the free thiol (in the case of sulfenyl chloride) or by cross-oxidation (in the case of p-nitrothiophenol or 2,2'-dithiobis(5-nitropyridine)). It is also envisioned that S-t-butylether, or similar protective groups, can also be successfully employed in this first step, because treatment of this tertiary-carbon thioether protecting group with 2,4-dinitrosulfenyl chloride should also yield the key intermediate, namely the asymmetrical disulfide.

In either case, a second delivery of an activator to the solid support is required in order to drive the deblock/activation reaction to completion, in other words, to form the desired asymmetrical disulfide, by either: (1) cross-oxidation (where the second activator is a iodine/p-nitrothiophenol reagent); or (2) by sulfenylation, (where the second activator is a arylsulfenyl chloride/triethylamine solution). These reagents are added to complete the formation of the desired asymmetrical disulfide from any residual undesired support-bound symmetrical disulfide or thiol moieties.

The next step in this solid phase synthetic scheme involves the coupling of the solid support-anchored disulfide with a monomeric nucleoside 3'-methylhydrogen-thiophosphonate or 3'-methylhydrogen-thiophosphonate synthons. These synthons are added concurrently with triethylamine or DBU solutions to generate the 5'-dithioate or 5'-thioate linkages, respectively.

Figure 6:
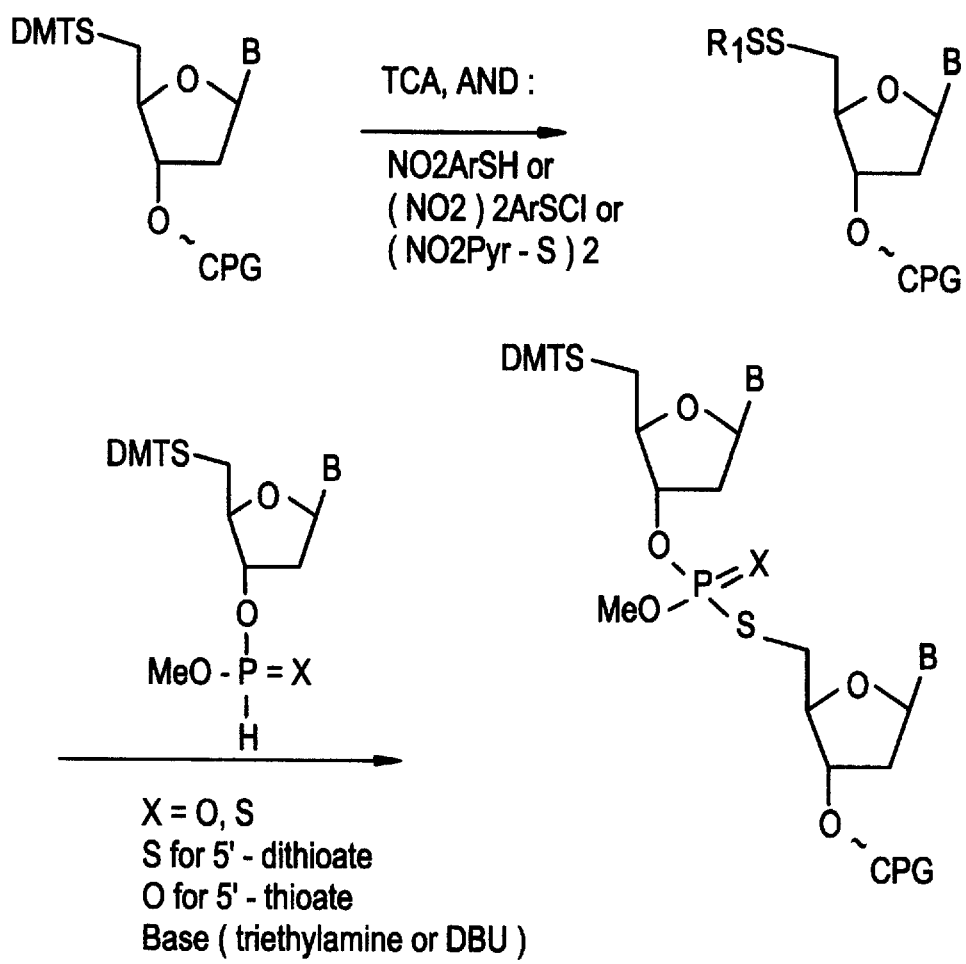
FIG. 6 shows the polymer-supported synthesis of dithio-modified internucleotide linkages in a 3'→5' direction using nucleoside 3'-methylhydrogenphosphonate intermediates (H-thiophosphonate method).

It is important to note that this method can be used for the synthesis of consecutive 5'-thioate (5'-thio-bridged) linkages, as well as 5'-dithioate linkages, by selecting the appropriate 3'-methylhydrogen-phosphonate synthon, either H-phosphonate for the first linkage or H-thiophosphonate in the latter case. FIG. 6 shows the polymer-supported synthesis of these internucleotide linkages through use of the 3'-methylhydrogen-phosphonate intermediates described above. The synthesis is compatible with solid supports and linkers. Sarcosine linkers may be needed when using DBU, as it is known that the succinyl linkers commonly used may be cleaved by the use of this strong base. Under the conditions of the reaction described herein, DBU has not caused significant cleavage of the growing oligonucleotide chains from the support. For the synthesis of 5'-dithioate linkages, the triethylamine used is compatible with conventional linkers and supports.

A number of different modified linkages can be synthesized using the H-thiophosphonate method of the present invention. For example, this chemistry is compatible with existing solid phase synthesis of DNA, so that both modified (e.g., 5'-dithio) and unmodified (i.e., 5'-oxy) linkages can be introduced into the same oligonucleotide sequence. Where it is desired to introduce 5'-oxy linkages adjacent to 5'-dithioate linkages, the 2'-deoxy-5'-O-(4,4'-dimethoxytrityl)-3'-methylhydrogen-thiophosphonate would be used as the incoming H-thiophosphonate nucleoside monomer. Upon completion of the base catalyzed coupling reaction, the chemistry can then be switched to phosphoramidite coupling, using conventional phosphoramidite methods, in the same direction as it is most commonly used, namely 3'→5' for the desired unmodified ("wild type" or phosphodiester) linkages. In the case of phosphoramidite reagents, methyl-phosphoramidites, which are base stable, should be used in place of conventional 2-cyanoethyl-phosphoramidites, particularly where the phosphodiester internucleotide linkage(s) precede the formation of 5'-dithioate linkages in the growing oligonucleotide chain.

The H-thiophosphonate method of the present invention can be employed to synthesize 5'-dithio-modified oligonucleotides containing substitutions at other "bridging" or "non-bridging" positions of the internucleotide linkage. In this case, synthesis of a modified nucleoside 3'-hydrogenthiophosphonate synthon would commence using a modified nucleoside 3'-phosphoramidite.

The following examples are provided to aid in the understanding of the present invention, the true scope of which is set forth in the appended claims. It is understood that modifications can be made in the procedures set forth, without departing from the spirit of the invention.

Proton ($^1$H), phosphorus ($^{31}$P) and carbon ($^{13}$C) Nuclear Magnetic Resonance spectra were measured at 300 MHz, 121 MHz and 75 MHz, respectively in a General Electric Omega® 300NB spectrometer (General Electric Company, Fremont, Calif., currently supported by Bruker Instruments, Fremont, Calif.). Chemical shifts are reported using tetramethylsilane or the 7.24-ppm or 77.0-ppm resonance of residual chloroform in deuterated solvent as internal reference for proton and carbon, respectively. Chemical shifts for phosphorus are reported relative to an external reference of phosphoric acid (0 ppm). For NMR sample preparation analysis, the following deuterated solvents were used: d-chloroform ($CDCl_3$); deuterium oxide ($D_2O$); and, when needed, d3-methanol ($CD_3OD$) and d6-dimethyl sulfoxide (DMSO-$d_6$).

All reactions were conducted in oven-dried glassware under an atmosphere of dry argon. Unless otherwise specified, the best quality anhydrous solvents and reagents were obtained from commercial sources. The following reagents were purified before use: methylene chloride ($CH_2Cl_2$), pyridine, triethylamine and acetonitrile were distilled from calcium hydride ($CaH_2$); diisopropylethylamine, N,N-dimethylformamide and dimethyl sulfoxide (DMSO) were dried over activated 4 Å molecular sieves; methanol was dried by distillation from magnesium turnings/iodine; tetrahydrofuran was distilled from sodium/benzophenone ketyl; d-chloroform (CDCl$_3$) was dried by passage through basic alumina (Woelm, Activity I) just prior to use. Bis-pyrrolidino 2-cyanoethoxyphosphine was prepared by reacting commercially available 2-cyanoethoxy-dichlorophosphine with 1'-trimethylsilyl pyrrolidone (2 equivalents) in anhydrous ether at 0° C. After filtration and removal of volatiles in vacuo the bis-pyrrolidino 2-cyanoethoxy phosphine (pure by $^{31}$P NMR) was stored at −78° C. until use.

Analytical thin-layer chromatography (TLC) was performed by using aluminum sheets coated with a 0.20-mm layer of silica gel 60 containing PF 254 indicator (Merck, no. 5554). Flash chromatography was performed by the method of Still (Still, et al., *J. Org. Chem.*, 34, 2923 (1978) using Merck 230 to 400-mesh silica gel 60 (Merck No. 9385-9).

Example 1

Synthesis of 5'-deoxy-S-(acetyl)-5'-deoxythymidine

This example demonstrates the synthesis of 5'-deoxy-5'-S-acetyl-5'-deoxythymidine. 5.8 g of thymidine (23.9 mmol) was azeotropically dried by co-evaporation with freshly distilled pyridine (twice with 100 mL) and anhydrous toluene (twice with 50 mL), followed by drying in vacuo overnight. A solution of triphenylphosphine (8.178 g, 31 mmol) in 75 mL of freshly distilled tetrahydrofuran (THF) was cooled to 0° C. under argon over a period of 40 minutes with stirring. Diisopropyl azodicarboxylate (6.2 mL, 31.5 mmol) was added to the cooled solution. The resulting white suspension of the triphenylphosphine-diisopropyl azodicarboxylate complex was stirred for 45 minutes at 0° C. A solution of thymidine (5.8 g, 23.9 mmol) in 55 mL of anhydrous N,N-dimethylformamide (DMF) and 10 mL of THF was added to the stirred suspension, followed by thiolacetic acid (2.2 mL, 31 mmol), resulting in the white suspension turning to a pale yellow solution. This solution was stirred for 2½ hours in an ice bath, after which all of the solvents were removed in vacuo, and the resulting deep red residue was purified by silica gel flash chromatography using a gradient of 0 to 6% MeOH in CH$_2$Cl$_2$. The fractions containing product were concentrated and dried to yield 3.55 g (11.79 mmol, 49% yield) of a white solid.

The product was characterized by $^1$H NMR and 2D-cosy to verify the identity of the desired compound.

Example 2

Synthesis of 5'-deoxy-S-(acetyl) 3'-O-(4,4'-dimethoxytrityl)5'-deoxythymidine

This example demonstrates the synthesis of 5'-deoxy-S-(acetyl)-3'-O-(4,4'-dimethoxytrityl)5'-deoxythymidine.

The 5'-deoxy-5'-S-(acetyl)5'-deoxythymidine from Example 1 (3.55 g, 11.79 mmol) was dried by co-evaporation with anhydrous pyridine (twice with 100 mL) and then re-dissolved in 80 mL of pyridine. The resulting 5'-deoxy-5'-(thiolacetyl)thymidine/pyridine solution was reacted with 4,4'-dimethoxytrityl chloride (DMTrCl) (5.2 g, 15.3 mmol) and 50 mg of 4-dimethylaminopyridine (DMAP). The reaction was followed by standard silica gel thin layer chromatography (TLC). After 16 hours of reaction time, an additional 2.0 g of DMTrCl was added (5.9 mmol). After stirring for 3 days under argon at ambient temperature, the pyridine was removed in vacuo and the residue was dissolved in CH$_2$Cl$_2$ (300 mL) and extracted with 150 mL of saturated aqueous NaHCO$_3$. The organic layer was dried with anhydrous sodium sulfate (Na$_2$SO$_4$), filtered and concentrated. The crude thiolacetate product was purified by silica gel flash chromatography using a gradient of 0 to 4% MeOH in CH$_2$Cl$_2$ to yield 7.0 g of pure product, pale yellow foam (98% yield)

The product was characterized by $^1$H NMR and 2D-cosy to verify the identity of the desired thiolacetate compound.

Example 3

Synthesis of 5'-deoxy-3'-O-(4,4'-dimethoxytrityl)5'-thiol thymidine

This example demonstrates the synthesis of 5'-deoxy-3'-O-(4,4'-dimethoxytrityl)5'-thiol thymidine.

The thiolacetate from Example 2 (1.59 g, 2.64 mmol) was dissolved in 300 mL of thoroughly degassed EtOH. The solution was cooled to 0° C. in an ice bath for 1 hour while bubbling argon through it. 8.6 mL of 10 N NaOH (aqueous, 86 mmol) were then added. The reaction was stirred at 0° C. for 3 hours and monitored by TLC. The product was visualized with Ellman's reagent (5% solution in 0.1M, pH 8 Tris buffer). The reaction mixture was then poured into 500 mL CHCl$_3$ and 200 mL saturated, aqueous NaHCO$_3$. The organic layer was dried over sodium sulfate (Na$_2$SO$_4$), filtered, and concentrated. The product was purified by silica gel flash chromatography using a gradient of 0 to 6% MeOH in CHCL$_3$ to yield 1.4 g ( 94% yield) of a white foam after drying in vacuo overnight. In order to avoid oxidation of the thiol to a disulfide, the compound was used within 24 hours of preparation.

The product was characterized by $^1$H NMR and 2D-cosy to verify the identity of the desired thiol compound. This thiol co-migrates in analytical silica gel TLC with the thiolacetate compound from Example 2 and also with the diisopropylamino phosphoramidite compounds described in Examples 4 and 5, below. However, the desired thiol compound can easily be detected on TLC by spraying with Ellman's reagent.

Example 4

Synthesis of 5'-deoxy-5'-S-[(2-cyanoethyl) pyrrolidino-phosphoramidite]-5'-deoxy-3'-O-(4,4'-dimethoxytrityl)thymidine This example demonstrates the synthesis of 5'-deoxy-5'-S-[(2-cyanoethyl)pyrrolidino-phosphoramidite]-5'-deoxy-3'-O-(4,4'-dimethoxytrityl)thymidine.

1.54 g (2.75 mmol) of the 5'-deoxy-3'-O-(4,4'-dimethoxytrityl)5'-thiol thymidine from Example 3 was azeotropically dried by co-evaporation with freshly distilled methylene chloride. Under argon, while stirring at room temperature, a solution of the mercapto-thymidine in 36 mL of CH$_2$CL2 (containing 2 granules of dried 4 Å sieves) was treated with 1.01 g (4.19 mmol) of bis-pyrrolidino-2-cyanoethoxyphosphine, and 15 mL of a 0.5M (7.5 mmol) solution of tetrazole (sublimed grade, Aldrich Chemical Company, Milwaukee, Wis.) in anhydrous acetonitrile. This reaction mixture was stirred under argon for exactly 5 minutes, when immediately poured into 300 mL of CH$_2$CL$_2$ containing 5% of triethylamine. The resulting solution was extracted quickly with 100 mL portions of saturated, aqueous NaHCO$_3$, aqueous 10% Na$_2$CO$_3$ and saturated, aqueous NaCl solutions. The organic layer was dried over anhydrous $Na_2SO_4$, filtered, and then concentrated to an oil. The oil was dissolved in 10 mL of $CH_2Cl_2$ and precipitated by slow, drop-wise addition into rapidly stirring, degassed heptane (1.3 L, containing 3% triethylamine). The white solid precipitate was collected by filtration and dried in vacuo to yield 1.479 g (2.02 mmol, 73% yield) of product. For long term storage, the dried solid was kept desiccated at −20° C.

The product was characterization by $^{31}P$ NMR, $^1H$ NMR and 2D-cosy to verify the identity of the desired phosphoramidite compound.

Example 5

Synthesis of 5'-deoxy-5'-S-[(2-cyanoethyl) -N,N-diisopropylamino-phosphoramidite]-5'-deoxy-3'-O-(4,4'-dimethoxytrityl)thymidine This example demonstrates the synthesis of 5'-deoxy-5'-S-[(2-cyanoethyl)-N,N-diisopropylamino-phosphoramidite]-5'-deoxy-3'-O-(4,4'-dimethoxytrityl)thymidine.

1.64 g (2.93 mmol) of the 5'-deoxy-3'-O-(4,4'-dimethoxytrityl)5'-thiol thymidine from Example 3 was dried by co-evaporation with freshly distilled $CH_2Cl_2$. The resulting white foam was dissolved in 13 mL of anhydrous $CH_2CL_2$ under argon. 2.83 mL (16.24 mol) of N,N-diisopropylethylamine were then added to the solution, followed by 1.2 mL (5.36 mmol) of chloro-(2-cyanoethoxy) -N,N-diisopropylaminophosphine. The reaction was stirred under argon at ambient temperature for 2 hours. 1.0 mL of ethanol was then added, after which the reaction mixture was diluted with 300 mL of ethyl acetate containing 5% triethylamine. The solution was extracted with 100 mL portions of saturated, aqueous $NaHCO_3$ and saturated, aqueous NaCl. The organic layer was dried over $Na_2SO_4$, filtered and evaporated. The residue was purified by silica gel flash chromatography, eluting with $CH_2CL_2$-hexanes-ethyl acetate-triethylamine 5:5:4:1 (v/v/v/v). Appropriate fractions were concentrated and dried to yield a clear oil (2.0 g, 89% yield). The oil was dissolved in 10 mL of anhydrous toluene and precipitated by slow, drop-wise addition into 370 mL of vigorously stirred, degassed heptane containing 3% triethylamine. The white solid precipitate was collected by filtration and dried in a vacuum desiccator to yield 1.49 g (1.96 mmol, 66%) of product. For long term storage, the product was kept in vacuum dessicator at room temperature.

The product was characterized by $^{31}P$ NMR, $^1H$ NMR, and 2D-cosy to verify the presence of the desired phosphoramidite compound.

Example 6

Synthesis of 2',5'-dideoxy-5'-S-(acetyl)-N-benzoyl-cytidine

This example demonstrates the synthesis of 2',5'-dideoxy-5'-S-(acetyl)-N-benzoyl-cytidine.

Following the procedure described in Example 1 for thymidine, an analogous reaction scheme was initiated for cytidine with 6.0 g of 5'-deoxy-N-benzoyl-2',5'-dideoxycytidine (18.05 mmol). 5.04 g (12.9 mmoles, 71% yield) of 2',5'-dideoxy-5'-S-(acetyl)-N-benzoyl-2',5'-dideoxy-cytidine were obtained.

The product was characterized by $^1H$ NMR and 2D-cosy to verify the identity of the desired compound.

Example 7

Synthesis of 2',5'-dideoxy-5'-S-(acetyl)-N-isobutyryl-guanosine

This example demonstrates the synthesis of 2',5'-dideoxy-5'-S-(acetyl)-N-isobutyryl-guanosine.

Following the procedure described in Example 1, the analogous reaction scheme was initiated with 6.32 g (17.98 mmol) of 2',5'-dideoxy-N-isobutyryl guanosine being used as a starting material to obtain 5.1 g (12.42 mmol, 69% yield) of 2',5'-dideoxy-5'-S-(acetyl)-N-isobutyryl-guanosine.

The product was characterized by $^1H$ NMR and cosy to verify the identity of the compound.

Example 8

Synthesis of 2',5'-dideoxy-5'-S-(acetyl)-N-benzoyl-3'-O-(4,4'-dimethoxytrityl)cytidine This example demonstrates the synthesis of 2',5'-dideoxy-5'-S-(acetyl)-N-benzoyl-3'-O-(4,4'-dimethoxytrityl) cytidine.

Following the procedure described in Example 2, 5.03 g (12.9 mmol) of 2',5'-dideoxy-5'-S-(acetyl)-N-benzoyl-cytidine (from Example 6) were used as a starting material to obtain 8.303 g (12 mmol, 93%) of 2',5'-dideoxy-5'-S-(acetyl)-N-benzoyl-3'-O-(4,4'-dimethoxytrityl) cytidine.

The product was characterized by $^1H$ NMR to verify the identity of the desired compound.

Example 9

Synthesis of 2',5'-dideoxy-5'-S-(acetyl)-3'-O-(4,4'-dimethoxytrityl)-N-isobutyryl-guanosine This example demonstrates the synthesis of 2',5'-dideoxy-5'-S-(acetyl)-3'-O-(4,4'-dimethoxytrityl)-N-isobutyryl-guanosine.

Following the procedure described in Example 2, 2.79 g (6.8 mmol) of 2',5'-dideoxy-5'-S-(acetyl)-N-isobutyryl-guanosine (from Example 7) were used to obtain 3.49 g (4.9 mmol, 72% yield) of 2',5'-deoxy-5'-S-(acetyl)-3'-O-(4,4'-dimethoxytrityl)-N-isobutyryl-guanosine.

The product was characterized by $^1H$ NMR to verify the identity of the desired compound.

Example 10

Synthesis of 2',5'-deoxy-N-benzoyl-3'-O-(4,4'-dimethoxytrityl)-5'-thiol-cytidine This example demonstrates the synthesis of 2',5'-deoxy-N-benzoyl-3'-O-(4,4'-dimethoxytrityl)-5'-thiol-cytidine.

Following the procedure described in Example 3, 2.43 g (3.51 mmol) of 2',5'-dideoxy-5'-S-(acetyl)-N-benzoyl-3'-O-(4,4'-dimethoxytrityl) cytidine (from Example 8) were used as a starting material to yield 2.2 g (3.38 mmol, 96% yield) of 2',5'-dideoxy-N-benzoyl-2',5'-deoxy-3'-O-(4,4'-dimethoxytrityl)-5'-thiol-cytidine.

In order to prevent oxidations of the thio to a disulfide, the compound was used within 24 hours of preparation.

The product was characterized by $^1H$ NMR and 2D cosy to verify the identity of the desired compound.

Example 11

Synthesis of 2',5'-dideoxy-3-O-(4,4'-dimethoxytrityl)-N-isobutyryl-5'-thiol-guanosine This example demonstrates the synthesis of 2',5'-dideoxy-3-O-(4,4'-dimethoxytrityl)-N-isobutyryl-5'-thiol-guanosine.

Following the procedure described in Example 3, 1.44 g (2.02 mmol) of 2',5'-dideoxy-5'-S-(acetyl)-3'-O-(4,4'- dimethoxytrityl)-N-isobutyryl-guanosine (from Example 9) were used to produce 1.3 g (95% yield) of 2',5'-dideoxy-3-O-(4,4'-dimethoxytrityl)-N-isobutyryl-5'-thiol-guanosine.

In order to prevent oxidation of the thiol to a disulfide, the compound was used within 24 hours of preparation.

The product was characterized by $^1$H NMR and 2D cosy to verify the identity of the desired compound.

Example 12

Synthesis of 2',5'-dideoxy-N-benzoyl-5'-S-(2-cyanoethyl)-pyrrolidino phosphoramidite-3'-O-(4,4'-dimethoxytrityl)-cytidine This example demonstrates the synthesis of 2',5'-dideoxy-3'-N-benzoyl-5'-S-(2-cyanoethyl)pyrrolidino phosphoramidite-O-(4,4'-dimethoxytrityl)-cytidine.

Following the procedure described in Example 4, with the exception that the reaction was allowed to proceed for 8 minutes, 2.3 g (3.5 mmol) of 2',5'-deoxy-N-benzoyl-3'-O-(4,4'-dimethoxytrityl)-5'-thiol-cytidine (from Example 10) were used to produce 2.52 g (88%) of 2',5'-dideoxy-N-benzoyl-5'-S-(2-cyanoethyl)pyrrolidino phosphoramidite-3'-O-(4,4'-dimethoxytrityl)-cytidine.

The resulting solid was kept desiccated at −20° C. for long term storage.

The product was characterized by $^1$H NMR, $^{31}$P NMR and 2D-cosy to verify the identity of the desired compound.

Example 13

Synthesis of 2.5'-dideoxy-N-benzoyl-5'-S-[(2-cyanoethyl)N,N-diisopropylamino-phosphoramidite] -2.5'-dideoxy-31'-O(4,4'-dimethoxytrityl)cytidine This example describes the synthesis of 2,5'-dideoxy-N-benzoyl-5'-S-[(2-cyanoethyl) N,N-diisopropylamino-phosphoramidite]-2,5'-dideoxy-3'-O-(4,4'-dimethoxytrityl) cytidine.

Following the procedure described in Example 5, 939 mg (1.445 mmol) of 2',5'-dideoxy-3'-O-(4,4'-dimethoxytrityl)-N-isobutyryl-5'-thiol-cytidine (from Example 10) were used to produce 600 mg (49% yield) of 2,5'-dideoxy-N-benzoyl-5'-S-[(2-cyanoethyl)N,N-diisopropylamino-phosphoramidite]-3'-O-(4,4'-dimethoxytrityl)cytidine.

The product was characterized by $^1$H NMR and $^{31}$P NMR to verify the identity of the desired compound.

Example 14

Synthesis of 2',5'-dideoxy-5'-S-[(2-cyanoethyl) pyrrolidino-phosphoramidite]-3'-O-(4,4'-dimethoxytrityl)N-isobutyryl-guanosine This example describes the synthesis of 2',5'-dideoxy-5'-S-[(2-cyanoethyl)pyrrolidino-phosphoramidite]-3'-O-(4,4'-dimethoxytrityl)N-isobutyryl-guanosine.

Following the procedure described in Example 4, with the exception that the reaction was allowed to proceed for 10 minutes, 1.01 g (1.5 mmol) of 2',5'-dideoxy-3-O-(4,4'-dimethoxytrityl)-N-isobutyryl-5'-thiol-guanosine (from Example 11) were used to produce 1.65 g (1.96 mmol, 96% yield) of 2',5'-dideoxy-5'-S-[(2-cyanoethyl)pyrrolidino phosphoramidite]-3'-O-(4,4'-dimethoxytrityl)N-isobutyrylguanosine.

The product was characterized by $^1$H NMR and $^{31}$P NMR to verify the identity of the desired compound.

Example 15

Synthesis of 2.5'-dideoxy-5'-S-[(2-cyanoethyl)N,N-diisopropylamino-phosphoramidite]-3'-O-(4,4'-dimethoxytrityl) guanosine This example describes the synthesis of 2,5'-dideoxy-5'-S-[(2-cyanoethyl)N,N-diisopropylamino-phosphoramidite]-3'-O-(4,4'-dimethoxytrityl) guanosine.

Following the procedure described in Example 5, 1.81 g (2.7 mmol) of 2',5'-dideoxy-3-O-(4,4'-dimethoxytrityl)-N-isobutyryl-5'-thiol-guanosine (from Example 11) were used to produce 760 mg (0.87 mmol, 32% yield) of 2,5'-dideoxy-5'-S-[(2-cyanoethyl)N,N-diisopropylamino phosphoramidite]-3'-O-(4,4'-dimethoxytrityl) guanosine.

The product was characterized by $^1$H NMR and $^{31}$P NMR to verify the identity of the desired phosphoramidite compound.

Example 16

Synthesis of Dithio-Modified Oligonucleotides According to Thiophosphoramidite Method This example describes polymer-supported synthesis of partially modified oligonucleotides (containing both unmodified (phosphodiester) and modified (5'-dithioate) linkages) according to the first preferred (thiophosphoramidite) method described herein.

Synthesis was carried out on an Applied Biosystems (ABI, Foster City, Calif.) model 394 synthesizer using commercially available 5'-nucleoside-CPG (from Glen Research, Sterling, Va.) in the 5'→3' direction at a 1 μmol scale. The following substitutions or additions were made to the reagent ports: 5'-phosphoramidites (from Glen Research) in ports 1–4; 5'-thiophosphoramidites in ports 5–8 (for instance, 5'-thiophosphoramidite of thymidine, e.g., from Examples 4 or 5, in port 8); port 10 had a freshly prepared 5% solution (w/v) of elemental sulfur ($S_8$) in 1:1 (v/v) carbon disulfide ($CS_2$)-pyridine, containing 6% triethylamine; port 20 contained carbon disulfide ($CS_2$); and port 15 had 0.02M iodine in tetrahydrofuran (THF)/pyridine/water (Glen Research) replacing the usual 0.1M iodine oxidation solution. The standard ABI cycle, 1 μm CE, was modified so that one extra trichloroacetic acid (TCA) addition was done, followed by $CH_2CL_2$ washes, followed by double consecutive couplings (250 second wait each) for each modified linkage or one 250 second coupling for phosphodiester. For modified linkages, sulfur oxidation preceded the capping step. Carbon disulfide wash was done before and after the sulfur oxidation to prevent clogging of the reagent lines.

For partially modified oligonucleotides (containing both phosphodiester and 5'-dithioate linkages), mixed chemistry cycles were written so that the 5'-phosphoramidites (ports 1–4, corresponding coupling times, $I_2$ oxidation) were used for the former (unmodified) linkage, and 5'-thiophosphoramidites (ports 5–8, double coupling, $S_8$ oxidation) were used for the latter (modified) linkage. At the end of the solid phase synthesis, the dimethoxytrityl protecting group of the last base was left on the oligonucleotide (DMT-on).

It is important to note that although iodine is known in the art to cleave P—S internucleotide bonds, under the solid phase synthesis conditions, the 0.01M $I_2$ in THF/pyridine/water reagent did not induce significant amounts of cleavage of the bond, thus allowing synthesis of consecutive 5'-dithioate linkages in partially modified oligonucleotides containing both modified and unmodified (phosphodiester) linkages.

Optimization of cycles was necessary. For best yields, a 0.15M solution of the pyrrolidino-thiophosphoramidites were used. The diisopropylamino thiophosphoramidites gave decreased yields relative to the more reactive pyrrolidino thiophosphoramidites. Yields were determined by HPLC analysis of 0.5 to 1.0 O.D. of DMT-on crude oligonucleotides.

Oligonucleotides were synthesized DMT-on. The oligonucleotides were cleaved from the solid support and the base and phosphate protecting groups were removed by treating the polymer-supported oligonucleotide with concentrated aqueous ammonia for 15 hours at 55° C. The supernatant was decanted and the solvents removed by evaporation in vacuo. The residue was kept basic by addition of 1 mL of 0.2M Tris, pH 8. The compounds were preparatively by reversed phase HPLC on a Hamilton PRP-1 (5 g or 10 g particle size, 7 mm by 150 mm column) using a 0 to 40% gradient of acetonitrile in 0.1M triethylammonium acetate (TEAA, 1% per minute, 0.75 mL or 1 mL/minute flow rates respectively for 5 g or 10 g columns) in a Waters (Waters Pharmaceutical Division, Marlborough, Mass.) 4000 diode array HPLC equipped with autosampler, pumps and gradient controller.

The fractions containing purified DMT-containing oligonucleotide were pooled and dried in vacuo. Detritylation was accomplished by treating the dry oligonucleotide with 0.5 mL of 80% aqueous acetic acid (1 hour at ambient temperature, 20 µL of 80% HOAc per $A_{260}$ O.D. of DMT-on oligo) followed by removing the acetic acid in vacuo. The residue was then dissolved in 1.0 mL of $H_2O$, extracted with ethyl acetate to remove 4,4'-dimethoxytrityl alcohol, and desalted on Sephadex® G50 (eluting with 10 mM triethylammonium bicarbonate or TEAB) to yield pure oligonucleotides after drying repeatedly from distilled water. The oligonucleotides were quantitated measuring the absorbance at 260 nm. The extinction coefficient of the oligonucleotide was calculated using published extinction coefficients of the component nucleoside bases at 260 nm.

The dried oligonucleotides were dissolved in 0.5 mL of deuterium oxide (D20) for NMR analysis. Characterization was performed by $^{31}$P NMR to verify the presence of the desired linkages synthesized. The 5'-dithioate linkage has a resonance at ∂ 72.7–73.2 ppm, while the unmodified phosphodiester linkage has a resonance of 0 ppm relative to external phosphoric acid ($H_3PO_4$) reference.

Figure 7:
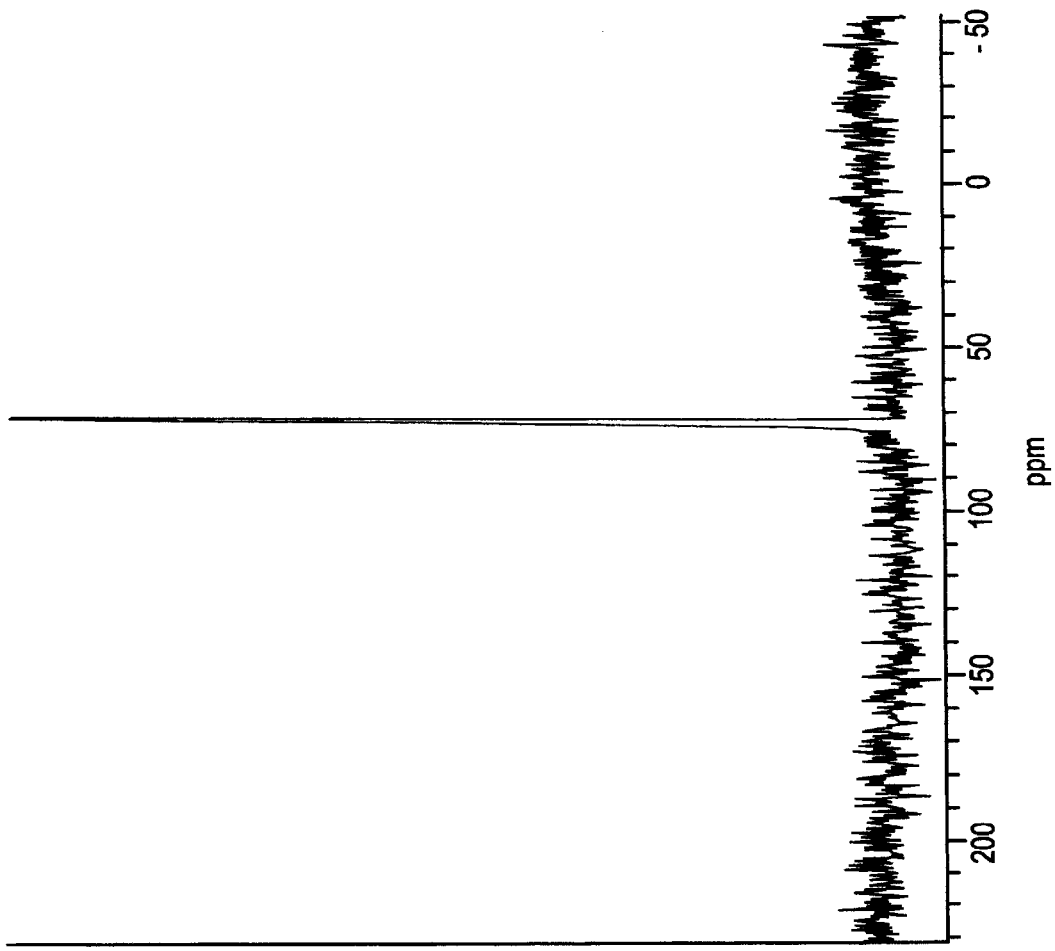
FIG. 7 shows the $^{31}$P NMR spectra of a fully modified polymeric thymine 18-mer oligonucleotide having all seventeen 5'-dithio-modified internucleotide linkages.

A completely modified T-18 oligonucleotide (a thymidine multimer containing all 5'-dithioate linkages) was synthesized and purified, as described in the above general procedure, resulting in 70 nmol of purified oligonucleotide (approximately 7% yield from 1 µmol starting CPG). The $^{31}$P NMR of the oligonucleotide in 0.5 mL $D_2O$ revealed only one broad peak at 72.7–73.2 ppm relative to external $H_3PO_4$ reference, as shown in FIG. 7. Polyacrylamide gel electrophoresis (15% PAGE) revealed one band when visualized with UV shadowing.

Partially modified oligonucleotides (containing both phosphodiester and 5'-dithioate linkages) were synthesized according to the procedures discussed above. The specific exemplary 11-mer modified oligonucleotides synthesized for internal radioactive labeling required for the nuclease stability assays described in Example 18, below, yielded the following amounts of oligonucleotide (following purification) from 1 µmol starting material.

TC CTG CTT TT*T    266 nmol
TC CTG CTT *T*T*T    230 nmol
TC CTG C*T*T *T*T*T    260 nmol (* represents 5'-dithioate linkage)

Figure 8:
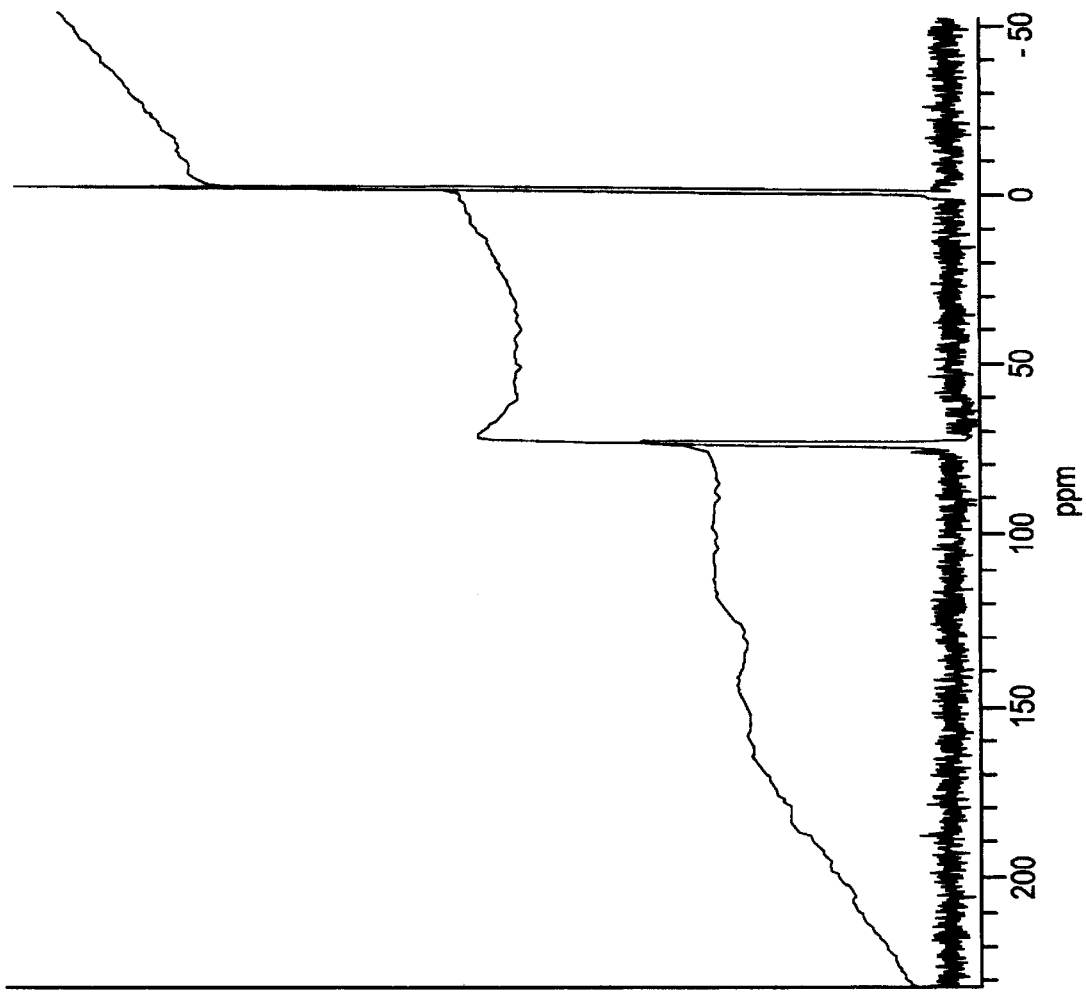
FIG. 8 shows the $^{31}$P NMR spectra of a partially modified 11-mer oligonucleotide having five 5'-dithio-modified internucleotide linkages at the 3'-end.

The $^{31}$P NMR of the last oligonucleotide is shown in FIG. 8.

Example 17

Preparation of Oligonucleotides for Nuclease Resistance Assays

The following series of oligonucleotides were synthesized for the purpose of testing for nuclease resistance:

TC CTG CTT TTT
TC CTG CTT TT*T
TC CTG CTT*T*T*T
TC CTG C*T*T*T*T*T (* represents 5'-dithioate linkage)

These four oligonucleotides were enzymatically phosphorylated according to published procedures using T4 polynucleotide kinase obtained from New England BioLabs (Beverly, Mass.) using γ$^{32}$P-adenosine triphosphate. (See Maxam et al. *Proc. National Acad. Sci. U.S.A.*, 74, 560–564 (1977)). The oligonucleotides were subjected to polyacrylamide gel electrophoresis. The polyacrylamide gel was scanned with a Phosphoimager® (Molecular Dynamics, Sunnyvale, Calif.) following published procedures. Johnston et al., *Electrophoresis II*, 355–360 (1990).

In order to assess the stability of the modified oligonucleotides, the kinased oligonucleotides were ligated separately to the following synthetic oligonucleotide:

TTT ATG GTC TT

The ligation reactions were performed according to published procedures using T4 DNA ligase obtained from New England BioLabs. (Maxam et al., *Proc. National Acad. Sci. U.S.A.*, 74, 560–564 (1977).) The template used in the ligation reaction was:

GCA GGA AAG ACC

The ligation products shown below were isolated from a 15% denaturing polyacrylamide gel according to published procedures. (Yansura et al. *Biochemistry* 16, 1772–1776, (1977).)

TTT ATG GTC TT#T CCT GCT TTT T
TTT ATG GTC TT#T CCT GCT TTT *T
TTT ATG GTC TT#T CCT GCT T*T*T *T
TTT ATG GTC TT#T CCT GC*T *T*T*T *T # represents $^{32}$P label
* represents 5'-dithioate linkage

During the ligation process, the radioactive phosphate atom becomes internalized within the ligation product. This eliminates loss of label due to phosphatase activity endogenous to the nuclease sources.

Example 18

Nuclease Resistance of 5'-Dithio-Modified Oligonucleotides

This example compares the nuclease resistance of various partially modified oligonucleotides of the present invention.

The internal $^{32}$P labeled oligonucleotides described in Example 17 containing zero ("wild type"), one, three and five 5'-dithioate modifications at the 3'-end of the oligonucleotide were used to determine nuclease resistance of partially modified 5'-dithioate oligonucleotides. The internally labeled oligonucleotides were analyzed for resistance to nuclease degradation from both: (1) nucleases endogenous to human serum; and, (2) snake venom phosphodiesterase, as described below.

A. Resistance to Endogenous Serum Nucleases 10 mL of whole blood was drawn by standard phlebotomy technique into a red top clot tube (Becton-Dickerson, Orangeburg, N.Y.). The blood was allowed to clot at room temperature for 30 minutes, and then the sample was centrifuged at 1000 rpm for 10 minutes. Serum was removed from the sample and 0.5 mL aliquots were prepared. Serum aliquots were stored at −70° C. and thawed immediately prior to use.

Figure 9:
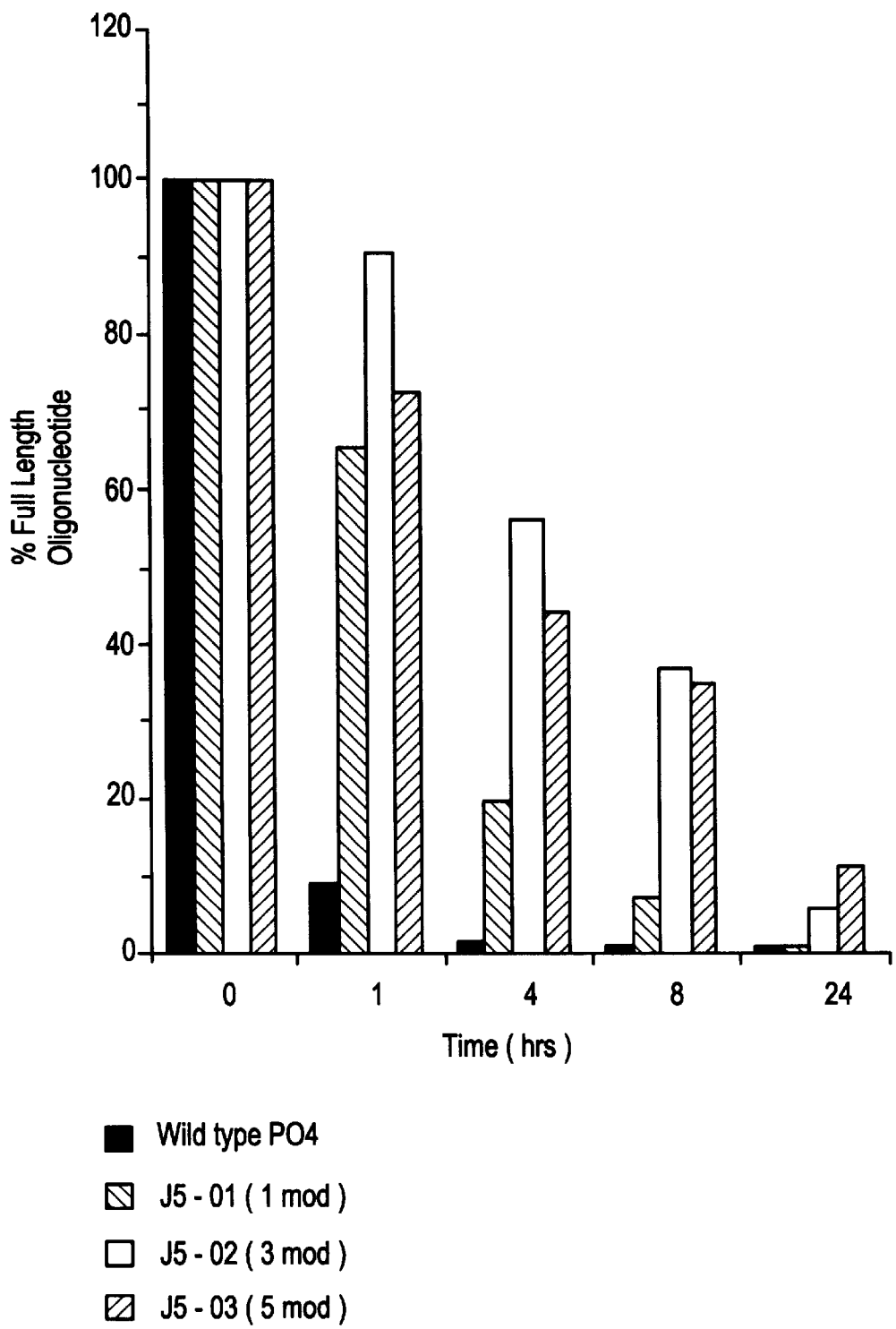
FIG. 9 is a graph showing comparative degradation rates of modified and unmodified oligonucleotides in the presence of serum.

The four gel-purified, internally labeled oligonucleotides described in Example 17 (19,000 cpm/pm stock solutions) were diluted to a concentration of 4 pm/μL. 12.5 μL of each oligonucleotide (50 pm) was incubated at 37 C. with 37.5 μl of human serum. The final oligonucleotide concentration was 1 μM in 75% (v/v) serum. 5 μL of mineral oil was added to prevent evaporation during the incubation. At timed intervals, 5 μL aliquots from each incubation were mixed with 10 μL formamide and 2 μL of 0.1% bromophenol blue/0.1% xylene cylanol in 80% formamide. The samples were stored at −20° C. until ready to analyze. The samples were boiled for two minutes, placed on ice for two minutes, and applied to a denaturing 20% polyacrylamide gel. Following electrophoresis, the gels were imaged and the amount of full length oligonucleotide was quantitated using a Phosphoimager®. The data obtained is shown in FIG. 9. Time points for the human serum stability assay were 0, 1 hr, 4 hr, 8 hr and 24 hr.

FIG. 9 shows stability of the oligonucleotides in the presence of serum graphed as the percentage of remaining full length oligonucleotide by integration of the full length band relative to the corresponding 0 time control lane. The data in FIG. 9 demonstrate that 5'-dithio-modified oligonucleotides are significantly more resistant to degradation in serum than unmodified "wild type" oligonucleotides. Even one 3'-dithioate modified linkage at the 3'-end showed some protection against nuclease degradation in a 1 hour exposure to human serum. Unmodified oligonucleotides were degraded more than 90% (with less than 10% full length oligonucleotide remaining) in the same 1 hour time interval, while 5'-dithioate oligonucleotides with a minimum of three modified linkages at the 3'-end were about 50% degraded in 4 hours. (See FIG. 9.)

B. Resistance to Snake Venom Phosphodiesterase

The four internally labeled oligonucleotides described in Example 17 were diluted separately to a concentration of 1 pm/μL in 0.2M sodium carbonate/sodium bicarbonate pH 9.5 buffer. Snake venom phosphodiesterase (Boehringer Mannheim) was diluted by mixing 2 μL of the enzyme as received with 123 μL of 0.2M sodium carbonate/sodium bicarbonate pH 9.5 buffer. 5 μL (5 picomoles) of each oligonucleotide solution was incubated with 5 μL of the Snake venom phosphodiesterase (SVPDE) solution at 37 C. The final concentration of oligonucleotide was 1 μM. For each time point a reaction was made, and at the end of the time intervals (0, 30 minutes, 60 minutes, 90 minutes or 120 minutes) each incubation mixture was mixed with 10 μL of dye in formamide solution, and stored at −20° C. until ready to analyze by 20% polyacrylamide gel electrophoresis. The gel was scanned, imaged, and the percent full length oligonucleotide was integrated using a Phosphoimager®.

Figure 10:
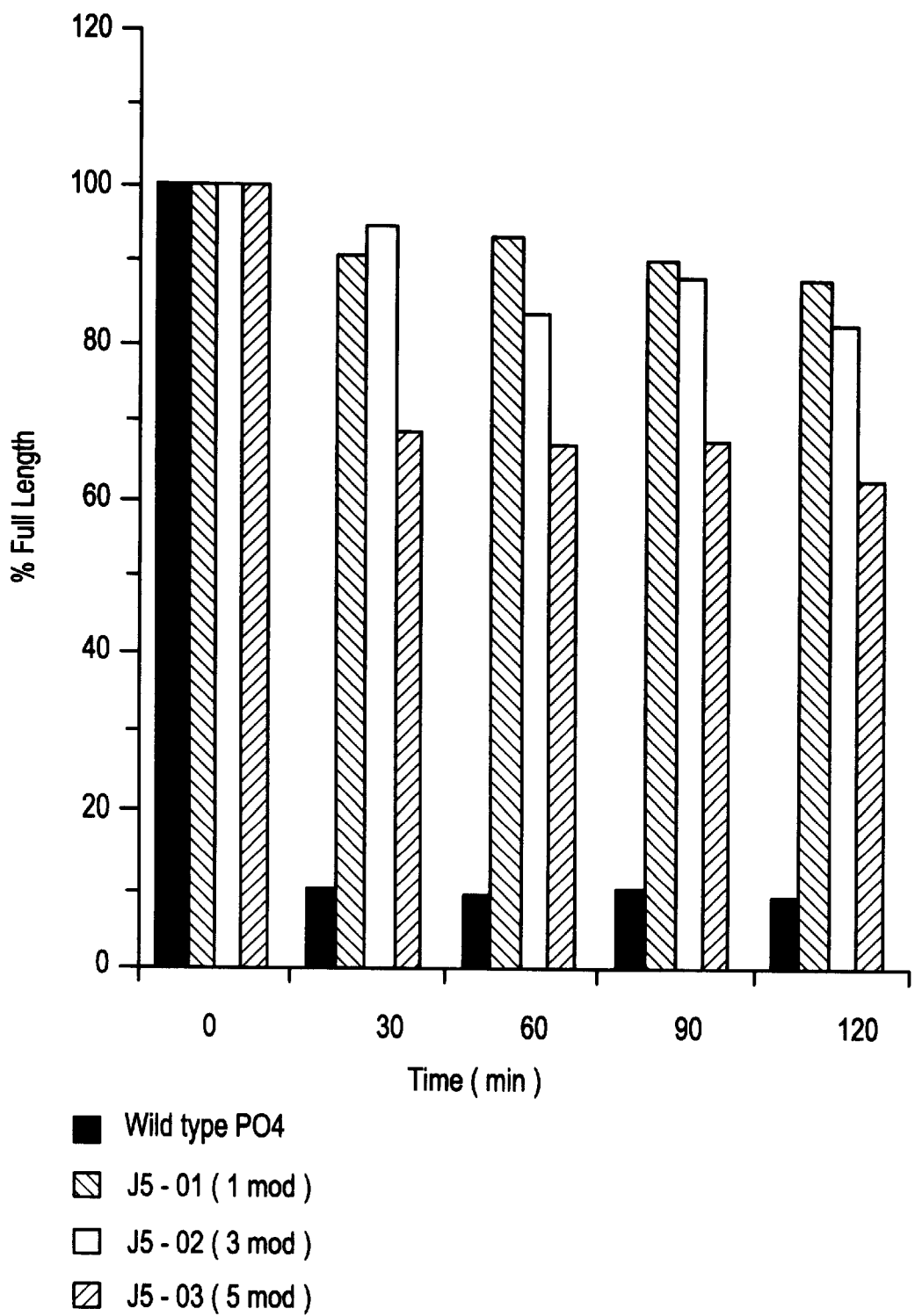
FIG. 10 is a graph showing comparative degradation rates of modified and unmodified oligonucleotides in the presence of snake venom phosphodiesterase.

FIG. 10 shows stability of the oligonucleotides in the presence of snake venom phosphodiesterase graphed as the percentage of remaining full length oligonucleotide by integration of the full length band relative to the corresponding 0 time control lane. At the concentration of SVPDE used, where wild type oligonucleotide is degraded 90% in 30 minutes, as little as a single dithioate linkage was found to confer substantial resistance to the nucleases present in snake venom phosphodiesterase. (See FIG. 10.)

C. Chemical Cleavage of 5'-Dithioate Oligonucleotides

The internally labeled oligonucleotides containing zero, one, three or five 5'-dithioate modifications (4 pm/μl stock solution) described in Example 17 were treated with 50 μM silver nitrate for 30 minutes, followed by 50 μM DTT, and then analyzed by PAGE, visualizing the bands using a Phoshoimager®. Cleavage was observed with the oligonucleotides containing modifications, versus no cleavage with the "wild type" control. This indicates that the 5'-dithio-modified linkage of the present invention can be used for specific manipulation of DNA, due to the specific chemical cleavage by silver (or mercury) ions of the 5'-dithioate modification of the present invention in the presence of phosphodiester or wild type linkages.

Example 19

Synthesis of 4,4'-dimethoxytrityl thiolacetate

This example demonstrates the synthesis of 4,4'-dimethoxytrityl thiolacetate.

25 g (73.8 mmol) of 4,4'-dimethoxytrityl chloride were dissolved in 500 mL of anhydrous methylene chloride. 15.8 mL (221 mmol) of thiolacetic acid was then added to the 4,4'-dimethoxytrityl chloride solution. The reaction was stirred for 30 minutes at ambient temperature, after which the excess acid was neutralized by slow addition of 30.8 mL (221 mmol) of triethylamine. The reaction mixture was washed twice with 500 mL of 5% aqueous $NaHCO_3$, 500 mL of water, and 300 mL of saturated aqueous NaCl. The organic layer was dried over sodium sulfate, filtered and concentrated. The resulting dark brown oil was crystallized from methylene chloride/hexanes. The light tan crystals were collected by filtration and dried in vacuo to yield 26.4 g (94% yield) of product.

The product was characterized by $^1H$ NMR and $^{13}C$ NMR to verify the identity of the desired compound.

Example 20

Synthesis of 5'-deoxy-5'-S-(4,4'-dimethoxytrityl)-thymidine.

This example demonstrates the synthesis of 5'-deoxy-5'-S-(4,4'-dimethoxytrityl)-thymidine.

20 mL of freshly distilled methanol were added under argon to 1.18 g (51.5 mmol) of sodium. After allowing all of the sodium to react, the excess methanol was removed to yield sodium methoxide as a white solid. The sodium methoxide was dissolved in 50 mL of dimethyl sulfoxide and degassed by bubbling with argon for 1 hour. This solution was added via cannula to a solution of 15.56 g (41 mmol) of 4,4'-dimethoxytrityl thiolacetate from the previous example in 250 mL of degassed dimethyl sulfoxide. The reaction was stirred under argon bubbling for 30 minutes, then 13.58 g (34,4 mmol) of 5'-Q-tosyl thymidine (prepared as described by Reist, *J. Org. Chem.*, 29, 554–558 (1964)) was rapidly added. The reaction was stirred under argon overnight, then diluted with 300 mL of methylene chloride, after which it was extracted twice with 300 mL 5% aqueous $NaHCO_3$, once with 300 mL water and once with 300 mL saturated aqueous NaCl. The organic layer was dried over sodium sulfate, filtered and evaporated. The crude product was purified by silica gel flash chromatography using a gradient of 0 to 5% ethanol in chloroform to yield 18 g of pure product (94% yield) as a pale yellow foam.

The product was characterized by $^1$H NMR and $^{13}$C NMR to verify the identity of the desired compound.

Example 21

Synthesis of 5'-deoxy-3-O-[(N,N-diisopropylamino) methyl phosphoramidite]-5'-S-(4,4'-dimethoxytrityl) thymidine This example demonstrates the synthesis of 5'-deoxy-3'-O-[(N,N-diisopropylamino) methyl phosphoramidite] 5'-S-(4,4'-dimethoxytrityl)thymidine.

10 g (17.8 mmol) of 5'-deoxy-5'-S-(4,4'-dimethoxytrityl) thymidine from Example 20 were azeotropically dried by co-evaporation with anhydrous pyridine (3×100 mL) and toluene (2×100 mL). 100 mL of anhydrous $CH_2Cl_2$, 9.92 mL (71.2 mmol) of triethylamine and 4.16 mL (21.4 mmol) of chloro-(N,N-diisopropylamino)methoxyphosphine were then added to the dried solid. The reaction was allowed to proceed for 30 minutes at ambient temperature. An aliquot was analyzed by $^{31}$P NMR to verify the conversion to product (which has a chemical shift of 150 ppm). The reaction was diluted with methylene chloride and extracted twice with 100 mL of 5% aqueous $NaHCO_3$, once with 100 mL saturated aqueous NaCl, dried over sodium sulfate and concentrated. The crude product was purified by silica gel flash chromatography using 4:4:1:1 hexanes:methylene chloride:ethyl acetate: triethylamine to yield 10.9 g (85% yield) of pure product.

The product was characterized by $^1$H NMR and $^{31}$P NMR to verify the identity of the desired compound.

Example 22

Synthesis of 5'-deoxy-5'-S-(4,4'-dimethoxytrityl)-3'-(methylhydroaenthiophosphonate) thymidine This Example demonstrates the synthesis of 5'-deoxy-5'-S-(4,4'-dimethoxytrityl)-3'-(methylhydrogenthiophosphonate)thymidine.

1.0 g (1.38 mmol) of 5'-deoxy-3'-O-[(N,N-diisopropylamino) methyl phosphoramidite] 5'-S-(4,4'-dimethoxytrityl)thymidine from Example 21 was dissolved in 75 mL of freshly distilled methylene chloride under argon. Dry hydrogen sulfide gas ($H_2S$, dried by passage of the gas stream through traps containing powdered anhydrous calcium oxide and calcium sulfate) was bubbled through the reaction for 1 minute. 13.8 mL of a 0.5M solution of tetrazole in anhydrous acetonitrile was then added, and hydrogen sulfide bubbling resumed for 10 minutes. The reaction was then stirred for one hour and followed by TLC, with an aliquot being analyzed by $^{31}$P NMR (the product has a chemical shift of 72 ppm). To prevent release of $H_2S$ into the laboratory, the exhaust line for the reaction was fitted with a drying tube filled with calcium sulfate, followed by aqueous bleach and concentrated aqueous sodium hydroxide traps. After 1 hour, the reaction was purged with argon for 20 minutes to remove excess $H_2S$, diluted with methylene chloride, and then extracted twice with 75 mL of 5% $NaHCO_3$, dried over sodium sulfate, and evaporated. The crude product was first purified by silica gel flash chromatography using a gradient of 0 to 1% ethanol in chloroform. The chromatographed product was dried, dissolved in 5 mL toluene, and then precipitated by slow addition into 800 mL of rapidly stirring pentane. The solid was collected by filtration to yield 0.56 g (61%) of pure product.

The product was characterized by $^1$H NMR and $^{31}$P NMR to verify identity of the compound.

Example 23

Synthesis of 5'-O-(4,4'-dimethoxytrityl)-3'-(methylhydroaenthiophosphonate)thymidine This example demonstrates the synthesis of 5'-O-(4,4'-dimethoxytrityl)-3'-(methylhydrogenthiophosphonate) thymidine.

Following a procedure analogous to the one described in the previous example, 5 g (6.93 mmol) of 5'-O-(4,4'-dimethoxytrityl)-3'-O-[(N,N-diisopropylamino) methylphosphoramidite]thymidine (Glen Research) were used to obtain 2.489 g (56%) of product.

The product was characterized by $^1$H NMR and $^{31}$P NMR to verify identity of the compound.

Example 24

Synthesis of Dithio-Modified Oligonucleotides According to the H-thiophosphonate Method Solid phase synthesis of partially modified oligonucleotides containing both unmodified (phosphodiester) and modified (5'-dithioate) linkages were carried out on an Applied Biosystems (Foster City, Calif.) model 394 synthesizer using the H-thiophosphonate method previously described herein. Selected steps, usually involving thiol reagents, were carried manually in a ventilated hood. Unless otherwise noted, all reagents were purchased from Applied Biosystems, Glen Research (Sterling, Va.), or Aldrich Chemical Company (Milwaukee, Wis.). All solutions for solid phase synthesis were thoroughly degassed with argon before use.

As a first step, a nucleoside containing 5'-deoxy-5'-S-(4, 4'-dimethoxytrityl)-thymidine was attached to the CPG resin. The coupling of the 3'-hydroxyl of the nucleoside can be readily accomplished via methods known in the art. For the next experiments, the attachment was performed via phosphite coupling of the 5'-deoxy-3'-O-[(N,N-diisopropylamino) methoxy phosphoramidite] 5'-S-(4,4'-dimethoxytrityl)thymidine from example 21 to a T-CPG resin. The standard Applied Biosystems program 1 μm CE and standard phosphoramidite reagents were used for the phosphite coupling.

The following protocols were used to introduce a 5'-dithioate linkage using the solid-phase H-thiophosphonate method.

(A) A synthesizer program was written HPhos21 which included (in sequence) the following steps: (1) deblock/activation step with 2.5% trichloro acetic acid in methylene chloride solution containing 0.2M 2,4-dinitrosulfenyl chloride (port 15); followed by, (2) methylene chloride washes; then, (3) second activation step with concurrent delivery of 0.2M 2,4-dinitrosulfenyl chloride in $CH_2Cl_2$ solution and 0.5M triethylamine in $CH_2Cl_2$ solutions from ports 11 and 12, respectively (written as if it were a capping protocol); (4) $CH_2Cl_2$ washes; (5) coupling with a 0.2M solution of 5'-O-(4,4'-dimethoxytrityl)-3'-(H-thiomethoxyphosphonate) thymidine synthon (from Example 23) in $CH_2Cl_2$, with concurrent delivery of a solution of 0.5M triethylamine in $CH_2Cl_2$ (port 9); and, finally, (6) more washes.

(B) A synthesizer program HPhos23 was used to do the following steps in sequence: (1) deblock/activation step with 2.5% TCA/$CH_2Cl_2$ containing 1.0M of p-nitrothiophenol; (2) $CH_2Cl_2$ washes; (3) second activation step (manual delivery) which effects a delivery of saturated iodine solution in $CH_2Cl_2$ containing 1.0M p-nitrothiophenol, with a wait of 5 minutes; (4) $CH_2Cl_2$ washes; (5) coupling with the 0.2M solution of 5'-O-DMT-H-thiophosphonate synthon (from Example 22) in $CH_2Cl_2$, delivered from an amidite port, with concurrent delivery of a 0.5M solution of triethylamine in $CH_2Cl_2$ from port 9 of the synthesizer.

(C) The same synthesizer program (HPhos23) was used to perform the same steps as (A) except that the first deblock/activation solution was composed of 2.5% TCA in $CH_2Cl_2$ containing 0.2M of 2,2'-dithiobis(5'-nitropyridine).

According to the protocols herein described, the following trimer containing one modified linkage was synthesized:

T*TT (* represents 5'-dithioate linkage)

The resins containing the DMT-off trimers were first treated with thiophenol/triethylamine/dioxane (thiolate) solutions to remove the methyl protecting groups, followed by rinsing the support with diethyl ether and methanol. The air-dried solid support oligonucleotide was then treated with concentrated aqueous ammonia for 1 hour at room temperature to cleave the oligo from the resin. The ammonia was removed in vacuo, with the crude oligonucleotide being kept basic by addition of 1.0 mL of 0.2M Tris, pH 8 buffer.

The crude DMT-off oligonucleotides were purified by reversed phase HPLC on a 10 p Hamilton PRP–1 (7 mm×150 mm) column using a gradient of 0 to 40% acetonitrile in 0.1M triethylammonium acetate. The $^{31}$P NMR of the purified oligonucleotides gave a resonance at 72–73 ppm which reflects the 5'-dithioate internucleotide linkage, and 0 ppm for the phosphodiester linkage, in an integrated ratio of 1:1, which confirms the identify of the desired oligonucleotide compound.

Example 25

Synthesis of 2',5'-dideoxy-5'-S-(2,4-dinitrophenylsulfenyl)thymidine 2.0 g (3.57 mmol) of 5'-deoxy-5'-S-(4,4'-dimethoxytrityl) thymidine from Example 20 were dissolved in 400 mL of methylene chloride. 2 g (12.24 mmol) of trichloroacetic acid and 3.35 g (14.27 mmol) of 2,4-dinitrobenzenesulfenyl chloride were then added to the resulting solution, and the reaction mixture stirred for 0.5 hour at ambient temperature. The reaction mixture was then diluted with methylene chloride, extracted twice with aqueous 5% $NaHCO_3$, once each with water and saturated aqueous NaCl, then dried over sodium sulfate and filtered. Silica gel was added to the dried organic layer, after which the suspension was evaporated to dryness carefully under reduced pressure. The silica gel containing the adsorbed product was loaded as a free flowing powder to the top of a silica gel column pre-equilibrated with chloroform. The column was eluted with a gradient of 0 to 6% ethanol in chloroform to yield 0.91 g (56%) of pure product.

The product was characterized by $^1$H NMR and $^{13}$C NMR to verify identity of the compound.

Example 26

Solution

Synthesis of Dithio-Modified Dimers

This example describes the synthesis of a T*T dimer (* represents 5'-dithioate linkage) in solution.

A solution containing 19.7 mg (43 μmol) of the 2',5'-dideoxy-5'-S-(2,4-dinitrophenylsulfenyl)thymidine from Example 25 in 0.2 mL of pyridine was added to a solution of 25 mg (39 μmol) of 5'-O-(4,4'-dimethoxytrityl)-3'-(methylhydrogenthiophosphonate) thymidine from Example 23 in approximately 0.8 mL of deuterated benzene (benzene-d6). The resulting solution was placed in an NMR tube. Then 10.9 μL (78 μmol) of triethylamine was added. The $^{31}$P NMR spectra after 1 minute revealed complete conversion of the H-thiophosphonate to the protected T*T dimer (the 2'-dithioate linkage with the methyl protective group). The $^{31}$P NMR spectra of the starting H-thiophosphonate consists of resonance at 72.4 ppm and 72.1 ppm (two diastereomers). The $^{31}$P NMR of the protected dimer resonates at 96.8 and 95.8 ppm. Two peaks were observed because there are two 5'-dithioate diastereomers.

After 5 minutes, the reaction was diluted with 2 mL of ethyl acetate, extracted twice with 1 mL of aqueous 5% $NaHCO_3$ and once with saturated aqueous sodium chloride. The organic layer was dried over sodium sulfate, filtered and concentrated. The dried dimer was dissolved in deuterated N,N-dimethylformamide (d7-DMF), and the product was characterized by $^{31}$P NMR (resonates at 97.4, 96.8-ppm in d7-DMF).

The d7-DMF solution of the protected dimer was treated with thiolate solution to yield the deprotected T*T dimer. The product was characterized by $^{31}$P NMR (69.0 and 68.9-ppm in d7-DMF).

In a separate deblocking reaction, the dried protected dimer was treated with 1 mL of a thiophenol:triethylamine:dioxane solution (2:2:1). The reaction yielded the deprotected T*T dimer in approximately 2 hours (chemical shift 72.9, 72.5 in the thiolate solution) The $^{31}$P NMR was run without a deuterium lock.

What is claimed is:

1. A method of synthesizing a modified internucleotide linkage having a sulfur substitution at the 5'-position of said internucleotide linkage comprising the steps of:
   (a) creating an asymmetrical disulfide at the 5'-position of a nucleoside;
   (b) reacting said asymmetrical disulfide of said nucleoside with a 3'-H-phosphonate synthon.

2. The method of claim 1 wherein said nucleoside is bound to a polymer support through the 3'-position of said nucleoside.

3. The method of claim 1 wherein said asymmetrical disulfide is created by reacting said polymer-supported nucleoside with acid in the presence of arylsulfenyl chloride.

4. The method of claim 3 wherein said nucleoside is a 2',5'-dideoxy-5'-S(4,4-dimethoxytrityl) nucleoside.

5. The method of claim 1 wherein said 3'-H-phosphonate synthon is a 3'-methylhydrogen-thiophosphonate synthon.

6. The method of claim 4 wherein said 3'-H-phosphonate synthon is a 3'-methylhydrogen-thiophosphonate synthon.

7. The method of claim 1 wherein said nucleoside is a 2',5'-dideoxy-5'-S(4,4'-dimethoxytrityl) nucleoside and said 3'-H-phosphonate synthon is a 3'-methylhydrogen-thiophosphonate synthon.

* * * * *

UNITED STATES PATENT AND TRADEMARK OFFICE
CERTIFICATE OF CORRECTION

PATENT NO. : 5,864,031
DATED : January 26, 1999
INVENTOR(S) : Russo-Rodriguez et al.

It is certified that error appears in the above-indentified patent and that said Letters Patent is hereby corrected as shown below:

Title Page [54], Line 1 and col. 1, line 1, change "5-Dithio" to --5'-Dithio--.

Title Page [56] "Cook", change "Monesters" to --Monoesters--.

Title Page [56] "Vyle", change "3'-Phosphorothiolate" to --3'-S-Phosphorothiolate--.

Column 1, Line 1, change "5-Dithio" to --5'-Dithio--.

Column 2, Line 34, change "inter-nucleotide" to --internucleotide--.

Column 9, Line 2, replace "the less" to --2', 5'-dideoxy-5'-S- --.

Column 15, Line 9, change "1'-trimethylsilyl" to --1-trimethylsilyl--.

Column 16, Line 58, change "$CH_2CL2$" to --$CH_2CL_2$--.

Column 19, Line 32, change "2.5'-dideoxy" to --2, 5'-dideoxy--.

Line 34, change "-2.5'-dideoxy-31'-O(" to -- -2, 5'-dideoxy-3'-O-(--.

Column 20, Line 2, change "2.5'-dideoxy" to --2, 5'-dideoxy--.

Column 21, Line 17, change "5 g or 10 g" to --5 µ or 10 µ--.

Line 21, change "5 g or 10 g" to --5 µ or 10 µ--.

Line 43, change "D20" to --$D_2O$--.

Column 24, Line 62, change "5'-Q-tosyl" to --5'-O-tosyl--.

UNITED STATES PATENT AND TRADEMARK OFFICE
CERTIFICATE OF CORRECTION

PATENT NO. : 5,864,031
DATED : January 26, 1999
INVENTOR(S) : Russo-Rodriguez et al.

It is certified that error appears in the above-indentified patent and that said Letters Patent is hereby corrected as shown below:

Column 25, Line 11, change "5'-deoxy-3-O-" to --5'-deoxy-3'-O- --.

Line 40, change "(methylhydroaenthiophosphonate)" to --(methylhydrogenthiophosphonate)--.

Column 26, Line 10, change "(methylhydroaenthiophosphonate)" to --(methylhydrogenthiophosphonate)--.

Column 27, Line 30, change "10 p" to --10 µ--.

Signed and Sealed this

Twenty-sixth Day of October, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 11 bases
( B ) TYPE: nucleic acid

```
        ( C ) STRANDEDNESS: single
        ( D ) TOPOLOGY: linear ( i i ) MOLECULE TYPE: other nucleic acid ( i i i ) SEQUENCE DESCRIPTION: SEQ ID NO:1:

TCCTGCTTTT T                                                                            11

( 2 ) INFORMATION FOR SEQ ID NO:2:

( i ) SEQUENCE CHARACTERISTICS:
        ( A ) LENGTH: 11 bases
        ( B ) TYPE: nucleic acid
        ( C ) STRANDEDNESS: single
        ( D ) TOPOLOGY: linear ( i i ) MOLECULE TYPE: other nucleic acid ( i i i ) SEQUENCE DESCRIPTION: SEQ ID NO:2:

TTTATGGTCT T                                                                            11

( 2 ) INFORMATION FOR SEQ ID NO:3:

( i ) SEQUENCE CHARACTERISTICS:
        ( A ) LENGTH: 12 bases
        ( B ) TYPE: nucleic acid
        ( C ) STRANDEDNESS: single
        ( D ) TOPOLOGY: linear ( i i ) MOLECULE TYPE: other nucleic acid ( i i i ) SEQUENCE DESCRIPTION: SEQ ID NO:3:

GCAGGAAAGA CC                                                                           12

( 2 ) INFORMATION FOR SEQ ID NO:4:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: other nucleic acid ( i i i ) SEQUENCE DESCRIPTION: SEQ ID NO:4:

TTTATGGTCT TTCCTGCTTT TT                                                                22
```